United States Patent
Andrews et al.

(10) Patent No.: US 11,713,442 B2
(45) Date of Patent: Aug. 1, 2023

(54) SYSTEM AND METHOD FOR CELL AND TISSUE PREPARATION

(71) Applicant: DEKA Products Limited Partnership, Manchester, NH (US)

(72) Inventors: Richard E. Andrews, Manchester, NH (US); Stephanie M. Miskell, Weare, NH (US); Zachary T. Kops, Watertown, MA (US); Justin M. Ferrentino, Mont Vernon, NH (US); Michael C. Tilley, Amherst, NH (US); Andrew K. Capulli, Auburn, NH (US); Keira L McGrath, Manchester, NH (US); Stuart A. Jacobson, Lexington, MA (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 358 days.

(21) Appl. No.: 16/904,198

(22) Filed: Jun. 17, 2020

(65) Prior Publication Data
US 2020/0392450 A1    Dec. 17, 2020

Related U.S. Application Data

(60) Provisional application No. 62/862,379, filed on Jun. 17, 2019.

(51) Int. Cl.
*C12M 1/36* (2006.01)
*B01L 3/00* (2006.01)
(Continued)

(52) U.S. Cl.
CPC ......... *C12M 41/48* (2013.01); *B01L 3/50273* (2013.01); *B01L 9/06* (2013.01);
(Continued)

(58) Field of Classification Search
None
See application file for complete search history.

(56) References Cited

U.S. PATENT DOCUMENTS

| 5,998,217 | A  | 12/1999 | Rao et al. |
| 6,786,054 | B2 | 9/2004  | Voute et al. |

(Continued)

FOREIGN PATENT DOCUMENTS

| CN | 201045139 Y   | 9/2016  |
| WO | WO 2003/087292 | 10/2003 |

(Continued)

OTHER PUBLICATIONS

International Search Report, Intl. App. # PCT/US2020/038214, dated Sep. 16, 2020.

(Continued)

*Primary Examiner* — Matthew D Krcha
(74) *Attorney, Agent, or Firm* — McCormick, Paulding & Huber PLLC

(57) ABSTRACT

Manufacturing system and method for creating multiple tissue constructs from cells. System can include a thaw subsystem (if the cells are provided in a frozen state), an expansion subsystem, a concentration subsystem, and a tissue maturation subsystem. Each of these subsystems is modular and can be reconfigured, and the process can be repeated depending on the specific tissue process being implemented. Multiple tissue types can be combined in multiple bioreactors. The activities of multiple bioreactors can be coordinated and controlled in an automated manner by a supervisor controller. The supervisor controller can receive user input at the start of the process, and can manage the process henceforth, alerting the user if user actions are required.

18 Claims, 27 Drawing Sheets

(51) Int. Cl.
| | |
|---|---|
| B01L 9/06 | (2006.01) |
| C12M 3/06 | (2006.01) |
| C12M 1/00 | (2006.01) |
| C12M 1/26 | (2006.01) |
| C12M 1/12 | (2006.01) |
| C12M 1/02 | (2006.01) |
| C12M 1/34 | (2006.01) |
| G01N 35/00 | (2006.01) |
| G01N 35/10 | (2006.01) |

(52) U.S. Cl.
CPC ............ *C12M 23/16* (2013.01); *C12M 29/00* (2013.01); *C12M 33/10* (2013.01); *C12M 37/00* (2013.01); *C12M 41/18* (2013.01); *C12M 41/36* (2013.01); *C12M 41/44* (2013.01); *C12M 45/20* (2013.01); *G01N 35/00732* (2013.01); *G01N 35/1004* (2013.01); *G01N 35/1079* (2013.01); *B01L 2300/021* (2013.01); *B01L 2300/041* (2013.01); *B01L 2300/0609* (2013.01); *B01L 2300/1805* (2013.01); *B01L 2400/0475* (2013.01); *B01L 2400/06* (2013.01)

(56) References Cited

U.S. PATENT DOCUMENTS

| | | | |
|---|---|---|---|
| 6,945,056 | B2 | 9/2005 | Brown et al. |
| 6,996,995 | B2 | 2/2006 | Voute et al. |
| 7,353,658 | B2 | 4/2008 | Voute et al. |
| 2013/0102071 | A1* | 4/2013 | Pan ................. C12M 23/10 222/145.6 |
| 2013/0210130 | A1 | 8/2013 | Larcher et al. |
| 2016/0252537 | A1* | 9/2016 | Murali ............... C12N 5/069 435/325 |
| 2017/0175063 | A1* | 6/2017 | Smith ............... C12M 25/16 |
| 2018/0066218 | A1* | 3/2018 | Koike ............... C12M 23/50 |
| 2022/0154852 | A1 | 5/2022 | White et al. |

FOREIGN PATENT DOCUMENTS

| | | |
|---|---|---|
| WO | WO 2005/116186 | 12/2005 |
| WO | WO 2015/071829 | 5/2015 |
| WO | 2017032829 | 3/2017 |
| WO | 2020257335 | 12/2020 |
| WO | 2021003188 | 1/2021 |
| WO | 2022159959 | 7/2022 |

OTHER PUBLICATIONS

Akhyari et al., The Quest for an Optimized Protocol for Whole-Heart Decellularization: A comparison of Three Popular and a Novel Decellularization Technique and Their Diverse Effects on Crucial Extracellular Matrix Qualities, Tissue Engineering: Part C, vol. 17, No. 9, 2011, 12 pages.
Astero, ThawSTAR® Automated Cell Thawing System, White Paper, downloaded from Internet Apr. 12, 2019, 6 pages.
Brooks, EtherNet/IP: Industrial Protocol White Paper, Institute of Electrical and Electronic Engineers, EFTA 2001, Logix/NetLinx Technology Adoption Rockwell Automation Oct. 2001, 12 pages.
Chen et al., Development of a scalable suspension culture for cardiac differentiation from human pluripotent stem cells Elsevier—Stem Cell Research 15, 2015 pp. 365-375.
Elseberg et al., The Challenge of Human Mesenchymal Stomal Cell Expansion: Current and Prospective Answers, New Insights into Cell Culture Technology, May 10, 2017, 16 pages.
Eppendorf Dasgip® Parallel Bioreactor System by Eppendorf, SelectScience®, downloaded from the Internet Dec. 2, 2021, https://www.selectscience.net/products/eppendorf-dasgip-parallel-bioreactorsystem/? prodID=195298#tab-3, 5 pages.
Ferng et al., Acellular porcine heart matrices: whole organ decellularization with 3D-bioscaffold & vascular preservation. Journal of Clinical and Translation Research, 2017; 3(2) pp. 260-270.
Gilpin et al., Decellularization Strategies for Regenerative Medicine: From Processing Techniques to Applications, Hindawi, BioMed Research International, vol. 2017, Article ID 9831534, 13 pages.
Kitahara et al., Heterotopic transplantation of a decellularized and recellularized whole porcine heart, Interactive Cardiovascular and Thoracic Surgery 22, 2016, pp. 571-579.
Lee et al., Inverted orientation improves decellularization of whole porcine hearts, Elsevier—Act Biomaterialia, 49, 2017, pp. 181-191.
Lelovas, A Comparative Anatomic and Physiologic Overview of the Porcine Heart, Journal of the American Association for Laboratory Animal Science, vol. 53, No. 5, Sep. 2014, pp. 432-438.
Lu et al., Repopulation of decellularized mouse heart with human induced pluripopent stem cell-derived cardiovascular progenitor cells, Nature Communications DOI: 10.1038/ncomms337, Aug. 13, 2013, 11 pages.
Michl, et al., Evidence-based guidelines for controlling pH in mammalian live-cell culture systems, Communications Biology, 2019 2:144, 12 pages.
Momtahan et al., Automation of Pressure Control Improves Whole Porcine Heart Decellularization, Termis, Tissue Engineering: Part C, vol. 00, No. 00 Methods, Jun. 2015, 15 pages.
Ott et al., Perfusion-decellularized matrix: using nature's platform to engineer a bioartificial heart, Nature medicine, Jan. 13, 2008, 9 pages.
Place et al., Limitations of oxygen delivery to cells in culture: An underappreciated problem in basic and translational research, Elsevier, Free Radical Biology and Medicine 112, 2017, pp. 311-322.
Remlinger et al., Procedure for Decellularization of Porcine Heart by Retrograde Coronary Perfusion, Journal of Visualized Experiments, Dec. 2012, 70, e50059, 8 pages.
Sartorius Integrated Cell Culture Analyzer, Aug. 2021, 5 pages.
Sartorius, Ambr® 15 Cell Culture Generation 2, Advanced Microbioreactor System, 2020/03, 16 pages.
Science Direct, Barragán, Fermentative Production Methods, Biotransformation of Agricultural Waste and By-Products, 2016, 2 pages.
Science Direct, Clapp, et al., Upstream Processing Equipment, Biopharmaceutical Processing, 2018, 4 pages.
Science Direct, Duan et al., Bioreactor design for algae growth as a sustainable energy source, Reactor and Process Design in Sustainable Energy Technology, 2014, 2 pages.
Science Direct, Ellis, Two-and three-dimensional tissue culture bioprocessing methods for soft tissue engineering, Standardisation in Cell and Tissue Engineering, 2013, 1 page.
Science Direct, Fundamentals, The MBR Book (Second Edition), 2011, 1 page.
Science Direct, Kirkpatrick, Standardisation in Cell and Tissue Engineering, 2013, 1 page.
Science Direct, Show et al., Production of Biohydrogen from Microalgae, Biofuels from Algae, 2014, 5 pages.
Science Direct, Tandon et al., Bioreactors for Tissue Engineering, Biomaterials Science (Third) Edition, 2013, 1 page.
Science Direct, Wang et al., Handbook of Membrane Reactors: Fundamental Materials Science, Design and Optimisation, 2013, 5 pages.
Science Direct, Zhong et al., New Developments and Application in Chemical Reaction Engineering, Studies in Surface Science and Catalysis, 2006, 1 page.
Taylor et al., Decellularization of Whole Human Heart Inside a Pressurized Pouch in an Inverted Orientation, Journal of Visualized Experiments, DOI:10.3791/58123, Nov. 26, 2018, 1 page.
Taylor et al., Decellularization of Whole Human Heart Inside a Pressurized Pouch in an Inverted Orientation, Materials List, Journal of Visualized Experiments, DOI:10.3791/58123, Nov. 26, 2018, 1 page.
Taylor et al., Decellularization of Whole Human Heart Inside a Pressurized Pouch in an Inverted Orientation, Supplement, Journal of Visualized Experiments, DOI: 10.3791/58123, Nov. 26, 2018, 5 pages.

(56) References Cited

OTHER PUBLICATIONS

Wang et al., Development of Novel Bioreactor Control Systems Based on Smart Sensors and Actuators, Frontiers in Bioengineering and Biotechnology, Feb. 4, 2020, 15 pages.
International Preliminary Report on Patentability dated Dec. 30, 2021, issued in PCT Patent Application No. PCT/US2020/038214, 7 pages.
Communication dated Jan. 26, 2022, issued in European Patent Application No. 20736864.8, 3 pages.
International Search Report and Written Opinion dated May 23, 2022, issued in PCT Patent Application No. PCT/US2022/070265, 12 pages.
Office Action dated Jun. 6, 2022, issued in Chinese Patent Application No. 202220160610.8, 5 pages.
U.S. Appl. No. 29/758,774, filed Nov. 18, 2020.

\* cited by examiner

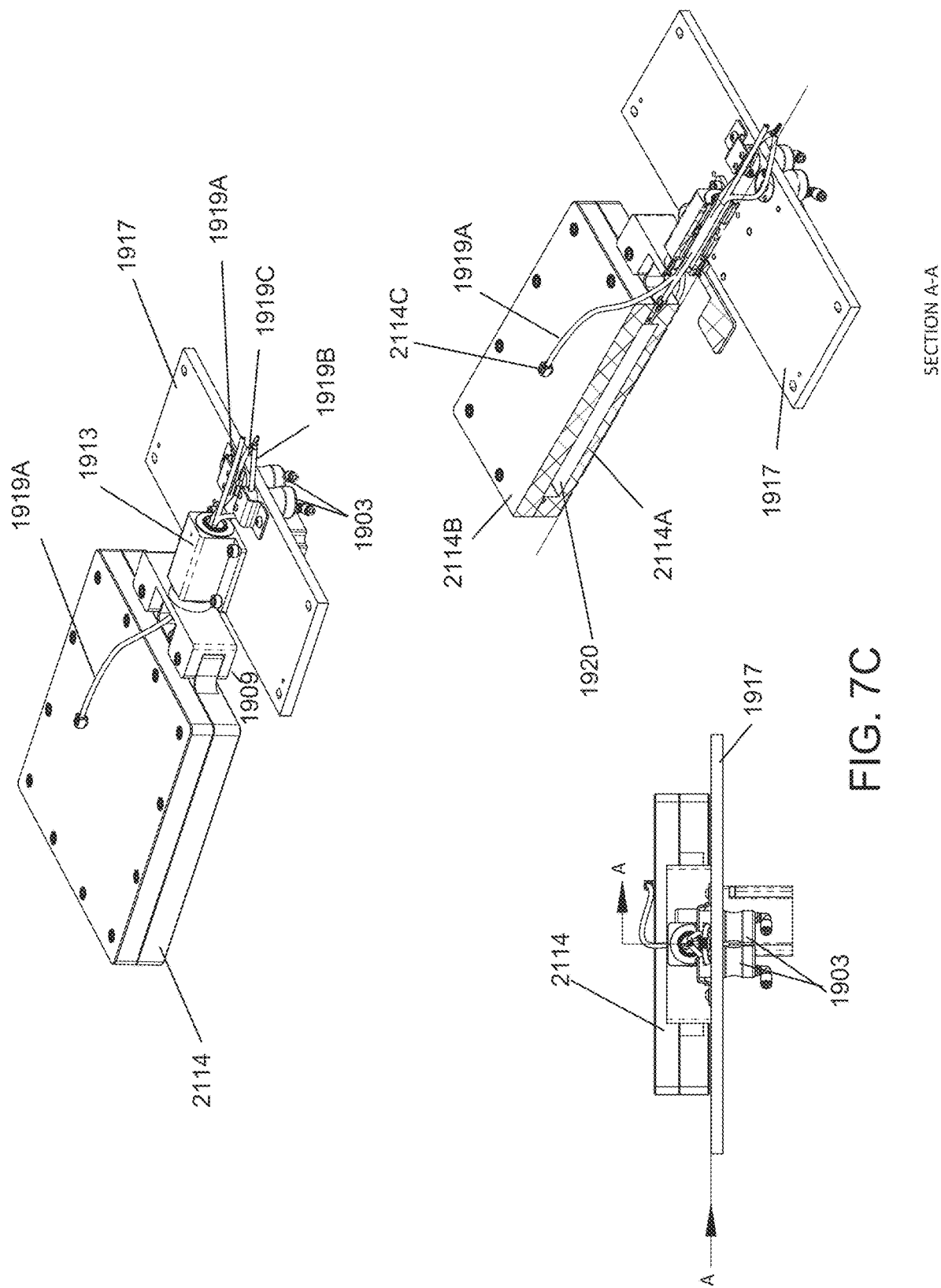

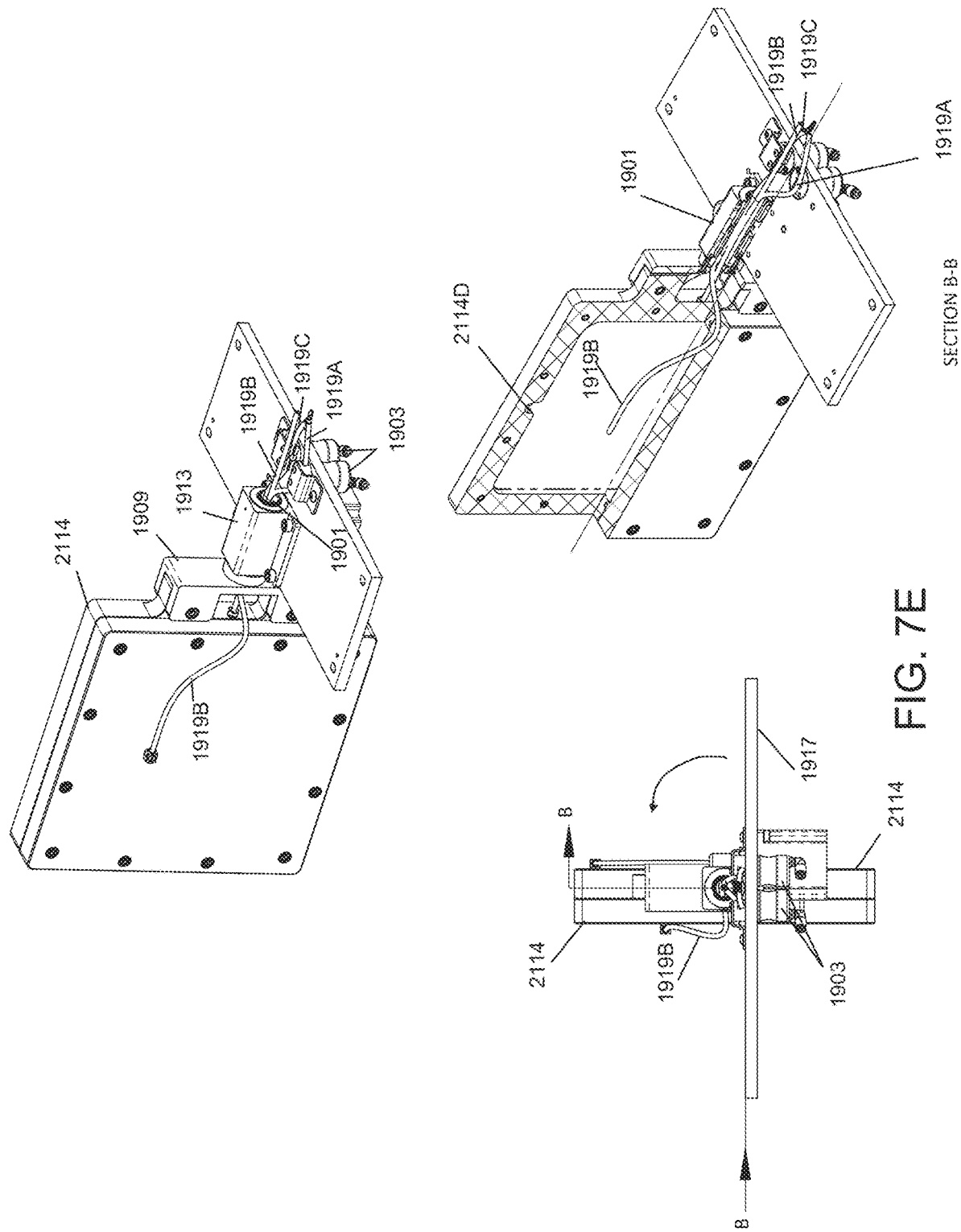

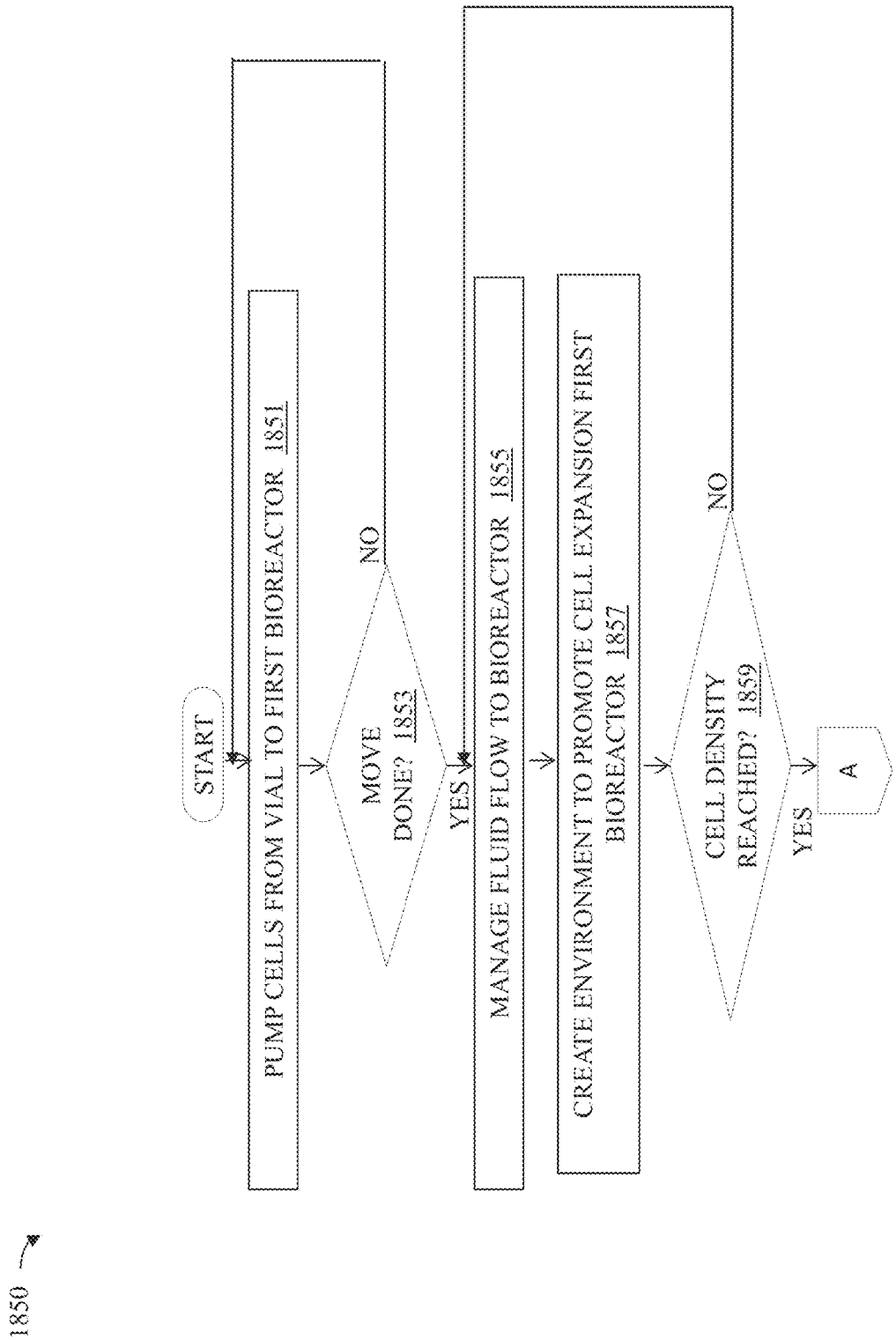

SYSTEM AND METHOD FOR CELL AND TISSUE PREPARATION

CROSS-REFERENCE TO RELATED APPLICATIONS

This utility patent application claims the benefit of U.S. Provisional Patent Application Ser. No. 62/862,379 filed Jun. 17, 2019, entitled System and Method for Cell Preparation, which is incorporated herein by reference in its entirety.

GOVERNMENT LICENSE RIGHTS

This invention was made with government support under W911NF-17-3-003, subaward F0008, awarded by Advanced Regenerative Manufacturing Institute. The government has certain rights in the invention.

BACKGROUND

The present disclosure pertains in general to tissue fabrication lines, and specifically to tissue fabrication lines that can automate multiple simultaneous instances of an allogeneic, allogeneic-like, and autologous tissue manufacturing processes. Single use components and non-invasive sensing can be used to support commercial scale-up in a non-environmentally controlled ISO "grey space" closed flow path.

Manual tissue fabrication in the laboratory has long been attempted. Methods used to fabricate typically suffer from non-repeatability or inconsistencies from one run to the next due to the skilled, manual nature of the work and the relatively poorly understood biological input materials. The current methods are typically highly labor intensive as well. However, the building blocks of tissue fabrication can include processes that can be automated. Among other things, automation can eliminate human error and improve consistency between production runs. Automation must include tying together of disparate processes that are needed to implement an entire fabrication line, and process initiation timing associated with the biological processes that can underlie tissue creation. Monitoring of specific characteristics that are indicative of the state of the tissue must be ongoing and fed back into a system activity control loop.

Tissue fabrication can occur in stages. If cells arrive frozen, they can be thawed. Cells arriving unfrozen, or thawed cells, can require expansion, concentration, and maturation steps. Typically, expansion occurs in flasks and static bioreactors located in incubators, and these require manual media exchanges. Typically, monitoring is visual and subjective. Transferring cells from one stage to the next is typically conducted manually.

If the process begins with frozen cells, proper thawing, if necessary, resuscitation, and storage of cells can aid in successful use of the cells. To thaw cells, a common manual method is to partially submerge the vials of cells into a 37° C. water bath. This manual method cannot meet automated manufacturing requirements, is highly subjective, and creates a risk of contamination, among other problems. A rapid thaw is essential to prevent ice crystallization during thaw. This is followed by a controlled 'quenching' of the media to dilute the cryoprotectant without causing the cell to swell too much (and pop). An automated system is able to better control the rapid thaw than manual processes. Cell cultures can be lost through accidents, contamination, age-related or environmentally-induced changes, and improper monitoring. When operating in a manual mode, cells would be visually monitored to assess level of confluence, any changes in media color, etc.

What is needed is a manufacturing line that can repeatedly and consistently create tissue automatically. What is needed is a system in which the processes that enable the stages are automated, and moving the cells from one stage to the next is also automated. What is needed is a system in which users are not determining when one stage has ended and another should begin, when cells need to be moved, and not performing the cell transfers manually. What is needed is a system that enables consistent results overall and avoids issues with cells/tissues being "ready" in the middle of the night or on weekends when users aren't monitoring them. What is needed is a system in which monitoring, and any feedback loop associated with monitored results, are fully automated. Such a line would be scalable so that the same automated process could be used to create many tissue constructs. The manufacturing line should consist of modular components, allowing reconfigurability based upon specific tissue process needs. The line should also be fluidically closed so that it can be operated in non-clean space without concerns of contaminating the cells and tissue contained therein.

SUMMARY

The system of the present teachings can include, but is not limited to including, a manufacturing line for producing tissue engineered medical products (TEMPs) or, more broadly, human cell, tissue, and cellular and tissue-based product (HCT/P). The manufacturing line can produce consistent results across tissue engineering runs, and can address safety and quality issues because human intervention during the cell maturation and incubation process is not necessary. The manufacturing line can include, but is not limited to including, stations in which cells are thawed, stations in which the thawed cells are expanded, stations in which expanded cells are concentrated, and stations in which concentrated cells incubate into tissue.

The method of the present teachings for enabling automatic manufacture of tissue can include, but is not limited to including, receiving cells in at least one vial, automatically pumping the cells from the at least one vial to at least one first bioreactor, automatically controlling fluid delivery from the at least one vial to the at least one first bioreactor when the cells are moved to the at least one first bioreactor, automatically creating a first pre-selected environment promoting expansion of the cells in the at least one first bioreactor, based on monitoring sensor data of critical process parameters, automatically harvesting the cells from microcarrier surfaces and quenching harvest enzymes, automatically pumping the expanded cells from the at least one first bioreactor to a concentrator when the expanded cells have reached a pre-selected density, automatically concentrating the expanded cells, automatically pumping the concentrated cells into the at least one first bioreactor when a pre-selected event has occurred, automatically pumping the cells from the at least one first bioreactor to at least one second bioreactor when the concentration cells are suspended, and automatically creating a second pre-selected environment promoting maturation of the concentrated cells into tissue in the at least one second bioreactor, based on sensor data of critical process parameters.

The method can optionally include automatically receiving and thawing cells including accessing an insulated container. The insulated container can house at least one vial of the frozen cells, and can include an insulated container lid and a vial holder. The method can further optionally include automatically controlling, by a thaw controller, removing the insulated container lid of the insulated container using a first gripper. The first gripper can be controlled by the thaw controller. The method can optionally include automatically determining, by the thaw controller, a location of the at least one vial within the vial holder, automatically controlling, by the thaw controller, positioning a second gripper at the location, and automatically controlling, by the thaw controller, removing the at least one vial from the insulated container using the second gripper. The second gripper can be controlled by the thaw controller. The method can include automatically controlling, by the thaw controller, returning the insulated container lid to the insulated container using the first gripper. The first gripper can be controlled by the thaw controller. The method can include automatically controlling, by the thaw controller, placing the removed at least one vial into a cell thawing device using the second gripper. The second gripper can be controlled by the thaw controller. The method can include automatically determining, by a thaw manager controlled by the thaw controller, when the frozen cells are thawed, and automatically controlling, by the thaw controller, removing the at least one vial of thawed cells using the second gripper. The second gripper can be controlled by the thaw controller. The method can include automatically controlling, by the thaw controller, transferring the at least one vial of thawed cells to a third gripper using the second gripper. The second gripper can be controlled by the thaw controller. The method can include automatically controlling, by the thaw controller, moving the at least one vial of thawed cells to a first pre-selected location using an actuator operably coupled to the third gripper, the actuator being controlled by the thaw controller. The method can include automatically controlling, by the thaw controller, decontaminating an exterior of the at least one vial by a decontaminating system, the decontaminating system being controlled by the thaw controller. The method can include automatically controlling, by the thaw controller, moving the at least one vial of thawed cells to a second pre-selected location for accessing using the actuator, the actuator being controlled by the thaw controller. The method can include automatically controlling, by the thaw controller, accessing, by an accessing system controlled by the thaw controller, the at least one vial, the accessing system including an accessing device, the accessing device being continuously energized during pumping operation. The method can include automatically controlling, by the thaw controller, pumping, by a pump controlled by the thaw controller, a solution into the at least one vial, automatically controlling, by the thaw controller, extracting, by means of advection, the thawed cells from the at least one vial, and automatically controlling, by the thaw controller, disposing of the at least one vial. The first gripper and the second gripper can optionally comprise a single device. The first gripper, the second gripper, and the third gripper can optionally comprise a single device. The method can optionally include automatically determining, by a first device controlled by the thaw controller, an identification of the removed at least one vial. The decontaminating system can optionally include decontaminating an exterior surface of the at least one vial. The solution can optionally include a neutralizing agent. The solution can optionally include media. Concentrating the expanded cells can optionally include centrifuging the expanded cells.

The system of the present teachings for enabling automatic manufacture of tissue can include, but is not limited to including, an expansion subsystem automatically pumping cells from at least one vial to at least one first bioreactor, the expansion subsystem automatically shutting valves from the at least one vial to the at least one first bioreactor when the cells are moved to the at least one first bioreactor, the expansion subsystem automatically creating a first pre-selected environment promoting expansion of the cells in the at least one first bioreactor, the expansion subsystem automatically pumping the expanded cells from the at least one first bioreactor to a concentrator when the expanded cells have reached a pre-selected density, the expansion subsystem configured to created resuspended cells from concentrated cells. The system can include a concentration subsystem automatically concentrating the expanded cells, and a maturation subsystem automatically pumping the resuspended cells into at least one second bioreactor when a pre-selected event has occurred, the maturation subsystem automatically creating a second pre-selected environment promoting maturation of the concentrated cells in the at least one second bioreactor based on monitoring sensor data of critical process parameters.

The concentration subsystem can optionally include a centrifugation device. The pre-selected event can optionally include detection of a desired concentration. The first pre-selected environment can optionally include a first growth media, the first growth media being continuously automatically adjusted based on monitoring sensor data of critical process parameters to maintain first pre-selected levels of growth media characteristics. The second pre-selected environment can optionally include second growth media, the second growth media being continuously automatically adjusted based on monitoring of sensor data of critical process parameters to maintain second pre-selected levels of growth media characteristics. The system can optionally include a thaw subsystem receiving frozen cells in at least one vial and automatically thawing the frozen cells.

The thaw subsystem can optionally include a thaw controller controlling the preparing of the cells, an insulated container station having a cooling means cooling an environment surrounding the frozen cells in the at least one vial, an insulated container maintaining the frozen cells at a pre-selected temperature range, and an insulated container lid retaining the environment, a lid gripper and a vial gripper, the lid gripper moving, under control of the thaw controller, the insulated container lid, the vial gripper moving, under control of the thaw controller, the at least one vial, at least one device locating, under control of the thaw controller, a position of each of the at least one vial, a thaw station receiving, from the vial gripper, under control of the thaw controller, the at least one identified vial, the thaw station including a thawing device housing the at least one identified vial, the thawing device thawing the cells within the at least one vial, the thaw station including a thaw station controller, under control of the thaw controller, the thaw station controller providing a status of the cells to the thaw controller, a decontamination station receiving, from the vial gripper, under control of the thaw controller, the at least one vial of thawed cells, the decontamination station including a means for decontaminating an exterior surface of the at least one vial of thawed cells, a puncture station receiving, from the vial gripper, under control of the thaw controller, the at least one decontaminated vial of thawed cells, the puncture station including at least two needles, the at least two needles puncturing, under control of the thaw controller, the decontaminated vial, a first needle of the at least two needles having a first length, a second needle of the at least two needles having a second length, the puncture station including a needle controller puncturing, under control of the thaw controller, the decontaminated at least one vial of thawed cells with the first needle, the first needle extending into the at least one decontaminated vial of thawed cells a first pre-selected distance, the needle controller puncturing, under control of a thaw manager, the decontaminated at least one vial of thawed cells with the second needle, the second needle extending into the at least one decontaminated vial of thawed cells a second pre-selected distance, and a solution pump pumping, under control of the thaw controller, solution from a solution reservoir through solution tubing and the first needle into the decontaminated at least one vial of thawed cells, the thawed cells being drawn through the second needle, the thawed cells flowing through cell tubing into a cell reservoir, the cells being removed from the decontaminated at least one vial of thawed cells creating at least one waste vial.

The system can optionally include an identification station identifying, under control of the thaw controller, each of the at least one vial. The first length can optionally include a longer length than the second length. The first pre-selected distance can optionally include a shorter distance than the second pre-selected distance. The system can optionally include a gas purge forcing substantially all contents of the decontaminated at least one vial to exit the decontaminated at least one vial. The decontamination station can optionally include a hood retaining decontamination fluids within a pre-selected area surrounding the identified at least one vial of thawed cells, a decontamination pump pumping, under control of the thaw controller, the decontamination fluids into the pre-selected area, and a nozzle directing the decontamination fluids towards the at least one identified vial of thawed cells. The puncture station can optionally include a base gripper maintaining the at least one identified vial in place while the needle controller, under control of the thaw controller, removes the first needle and the second needle. The system can optionally include a waste system receiving, from the vial gripper, under control of the thaw controller, the at least one waste vial after the needle controller removes the first needle and the second needle, the waste system depositing the at least one waste vial into a waste receptacle. The system can optionally include a hood surrounding the puncture station, the hood maintaining a controlled, clean volume surrounding the puncture station. The expansion subsystem can optionally include an expansion controller controlling a flow of cells from the thaw subsystem to the expansion subsystem, and a bioreactor controller monitoring and modifying the first pre-selected environment. The bioreactor controller can optionally include an agitation controller agitating the cells to encourage attachment of the cells to a surface, a temperature controller adjusting temperature of the at least one first bioreactor based on a pre-selected desired temperature, a gas mixing processor adjusting levels of gas in media surrounding the cells, the levels of gas based on pre-selected desired values of characteristics of the media, a monitoring process sensing values of the characteristics of the media, and a pump controller moving the media to and from the at least one first bioreactor. The characteristics can optionally include dissolved oxygen and pH. The the maturation subsystem can optionally include a media controller monitoring and modifying media before introducing the media to the second at least one bioreactor, and an incubator controller managing movement of the at least one second bioreactor, the incubator controller monitoring characteristics of the media in the at least one second bioreactor, the incubator controller flushing and restoring media from/to the at least one second bioreactor. The system can optionally include a media storage controller that can include a media level sensor monitoring an amount of media in a media reservoir, and a pump pressure sensor monitoring a pump moving media from the media reservoir to the media vessel.

Cells can be provided in any suitable way including, but not limited to, in frozen form. The method of the present teachings for preparing frozen cells for entering the manufacturing line of a tissue engineering system can include, but is not limited to including, accessing an insulated container. The insulated container can house at least one vial of frozen cells, and can include an insulated container lid and a vial holder. The insulated container can hold, and the system can accommodate, a single vial or multiple vials. The method can include automatically controlling the removal of the insulated container lid of the insulated container using a first gripper. The first gripper can be controlled by a thaw controller. The method can include automatically determining, by the thaw controller, a location of the at least one vial within the vial holder, automatically positioning, by the thaw controller, a second gripper at the location, and automatically removing the at least one vial from the insulated container using the second gripper. The second gripper can be controlled by the thaw controller. In some configurations, the actions of the first gripper and the second gripper can be performed by a single device. The method can include automatically controlling returning the insulated container lid to the insulated container using the first gripper. The method can include automatically determining, by a first device controlled by the thaw controller, and automatically controlling placing the removed at least one vial into a cell thawing device using the second gripper. The method can include automatically determining, by a thaw controller controlled by the thaw controller, when the frozen cells are thawed a pre-selected amount, and automatically controlling, by the thaw controller, removing the at least one vial of thawed cells using the second gripper. The method can include automatically controlling, by the thaw controller, transferring the at least one vial of thawed cells to a third gripper using the second gripper. The third gripper can be controlled by the thaw controller. In some configurations, the actions of the second gripper and the third gripper can be performed by a single device. In some configurations, the actions of the first gripper, the second gripper, and the third gripper can be performed by a single device. The method can include automatically controlling, by the thaw controller, moving the at least one vial of thawed cells to a first pre-selected location using an actuator operably coupled to the third gripper. The actuator can be controlled by the thaw controller. The method can include automatically controlling, by the thaw controller, decontaminating the at least one vial by a decontaminating system. The decontaminating system can be controlled by the thaw controller and can decontaminate the exterior surface of the vial. The method can include automatically controlling, by the thaw controller, moving the at least one vial of thawed cells to a second pre-selected location for puncturing using the actuator. The method can include automatically controlling, by the thaw controller, puncturing, by a puncturing system controlled by the thaw controller, the at least one vial, and automatically controlling, by the thaw controller, pumping, by a pump controlled by the thaw controller, a solution into the at least one vial. The method can include automatically controlling, by the thaw controller, extracting, by means of advection, the thawed cells from the at least one vial. The method can include automatically controlling, by the thaw controller, disposing of the vial. The solution can optionally include a buffer (PBS) neutralizing a freezing agent or media. The method can optionally include identifying the removed at least one vial.

The system of the present teachings for preparing cells for entering a tissue fabrication system can include, but is not limited to including, a thaw controller controlling the preparing of the cells, and an insulated container station. The insulated container station can include a cooling means cooling an environment surrounding the frozen cells in at least one vial, an insulated container maintaining the frozen cells at a pre-selected temperature range, and an insulated container lid retaining the environment. The system can include a lid gripper and a vial gripper. The lid gripper can move, under control of the thaw controller, the insulated container lid, and the vial gripper can move, under control of the thaw controller, the at least one vial. The system can include at least one device locating, under control of the thaw controller, and a position of each of the at least one vial. The system can include a thaw station receiving, from the vial gripper, under control of the thaw controller, the at least one identified vial. The thaw station can include a thawing device housing the at least one identified vial. The thawing device can thaw the cells within the at least one vial. The thaw station can include a thaw station controller, under control of the thaw controller. The thaw station controller can provide a status of the cells to the thaw controller. The system can include a decontamination station receiving, from the vial gripper, under control of the thaw controller, the at least one vial of thawed cells. The decontamination station can include a means for decontaminating the exterior surface of at least one vial of thawed cells. The system can include a puncture station receiving, from the vial gripper, under control of the thaw controller, the at least one decontaminated vial of thawed cells. The puncture station can include at least two needles. The at least two needles can puncture, under control of the thaw controller, the decontaminated vial. A first needle of the at least two needles can include a first length, and a second needle of the at least two needles can include a second length. The puncture station can include a needle controller puncturing, under control of the thaw controller, the decontaminated at least one vial of thawed cells with the first needle. The first needle can extend into the at least one decontaminated vial of thawed cells a first pre-selected distance. The needle controller can puncture, under control of the thaw controller, the decontaminated at least one vial of thawed cells with the second needle. The second needle can extend into the at least one decontaminated vial of thawed cells a second pre-selected distance. The system can include a solution pump pumping, under control of the thaw controller, solution from a solution reservoir through solution tubing and the first needle into the decontaminated at least one vial of thawed cells. The thawed cells can be drawn through the second needle, and can flow through cell tubing into a cell reservoir. The cells can be removed from the decontaminated at least one vial of thawed cells creating at least one waste vial.

The first needle length can optionally include a longer length than the second needle length. The first pre-selected distance in which the needle extends into the vial can optionally include a shorter distance than the second pre-selected distance in which the needle extends into the vial. The system can optionally include a gas purge forcing substantially all contents of the decontaminated at least one vial to exit the decontaminated at least one vial. The decontamination system can optionally include a hood retaining decontamination fluids within a pre-selected area surrounding the identified at least one vial of thawed cells, a decontamination pump pumping, under control of the thaw controller, the decontamination fluids into the pre-selected area, and a nozzle directing the decontamination fluids towards the at least one identified vial of thawed cells. The puncture station can optionally include a base gripper maintaining the at least one identified vial in place while the needle controller, under control of the thaw controller, removes the first needle and the second needle. The system can optionally include a waste system receiving, from the vial gripper, under control of the thaw controller, the at least one waste vial after the needle controller removes the first needle and the second needle. The waste system can optionally deposit the at least one waste vial into a waste receptacle. The system can optionally include a hood surrounding the puncture station that can maintain a controlled, clean volume surrounding the puncture station. The system can optionally include an identification station identifying, under control of the thaw controller, each of the at least one vial.

BRIEF DESCRIPTION OF THE DRAWINGS

The foregoing features of the disclosure will be more readily understood by reference to the following description, taken with reference to the accompanying drawings, in which:

FIG. 7C is a cross-sectional view of the rotational device of FIG. 7A coupled with a bioreactor in a first position;

FIG. 7E is a cross-sectional view of the rotational device of FIG. 7A coupled with a bioreactor in a third position;

FIGS. 9A and 9B are flowcharts of the method of the present teachings.

DETAILED DESCRIPTION

Figure 1:
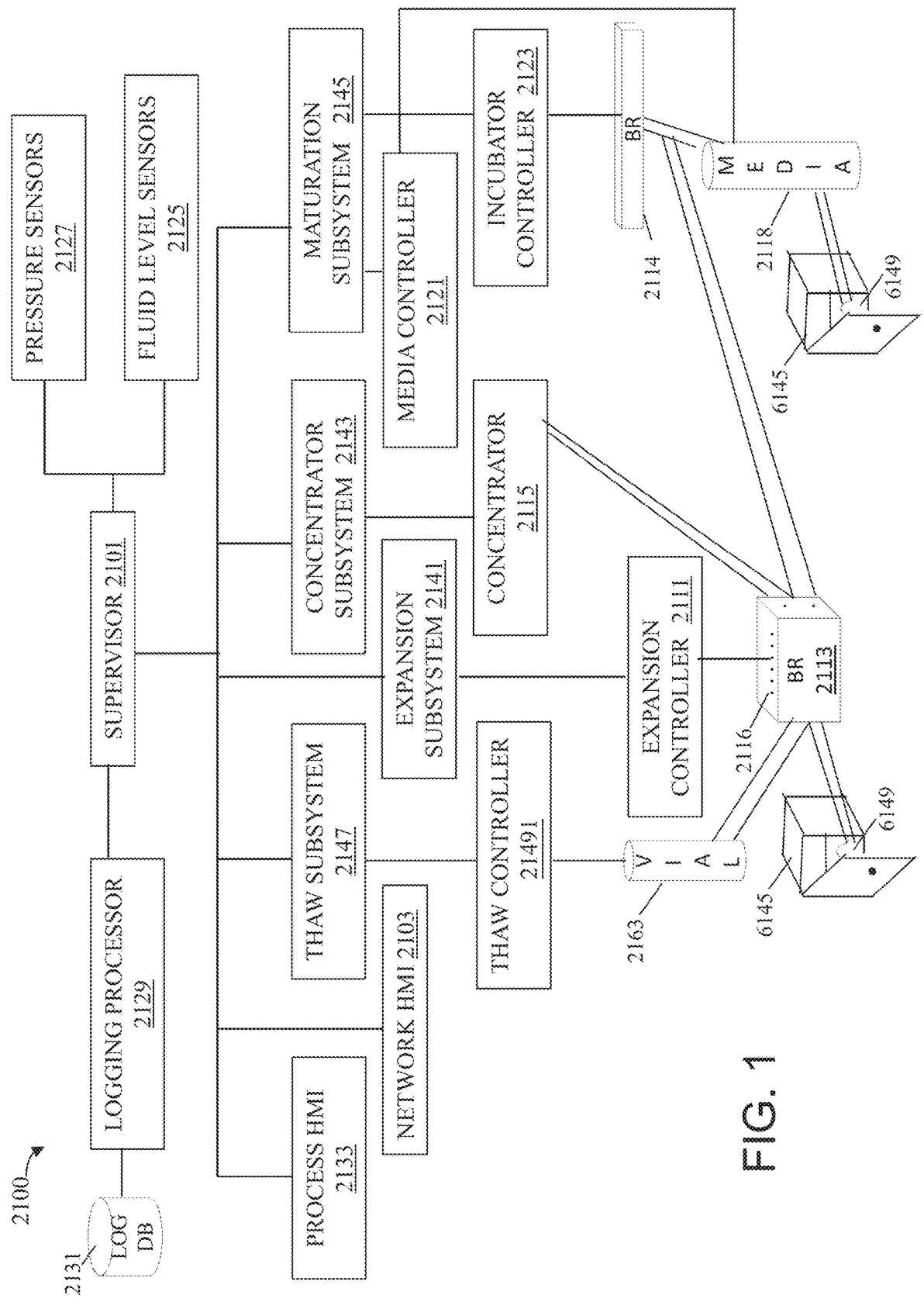
FIG. 1 is a schematic block diagram of the system of the present teachings.

The system of the present teachings for manufacturing tissue can enable a flexible process for creating tissue from cells. The flexible process can be implemented by a manufacturing production line. The system can remove the human component from the process after an initial setup and parameter specification, thus ensuring a reproducible result. The system can enable the interchangeability of parts along the production line by including a programmable controller that can follow a plug and play paradigm. The stations along the production line can be connected by sterilized tubing. The tubing can enable the movement of cells and fluid between stations on the line. Frozen cells can be thawed in the first station, and can be pumped, along with media, into bioreactor vessels containing nutritional fluid and housed in a controlled environment in the second station. The bioreactor vessels can include microcarriers, onto which cells can settle and attach or adhere as they are introduced to the bioreactor vessels. The microcarriers can be coated with a collagen, protein, or binding domain to promote cell attachment. Alternately, they can be chemically modified, electrically charged, or plasma treated to promote cell attachment. After initial cell seeding, culture on microcarriers can be maintained within the bioreactor with continuous sensing of culture parameters such as pH, dissolved oxygen, and temperature. The system can also control automated removal of spent media and introduction of fresh media throughout culture. When cell density has reached a pre-selected level, and when microcarriers, if present, have been separated from cells, or when cells have sufficiently digested the microcarriers, the proteins attaching the cells to the microcarriers, or the surface coating of the microcarriers, if necessary, the cells and liquid can be pumped to a third station in which the cells can be concentrated. In the third station, cells are separated from the majority of the neutralized digestion solution, cell culture media, and wash buffer, and then the cells, plus a pre-selected amount of the previous mixture, are moved to the expansion vessel to prepare them for maturation. At a pre-selected cycle time, for example, but not limited to, after resuspension at a desired concentration, the concentrated cells can be pumped into the fourth station that can include an incubator and media storage vessels. Through pumping and tubing, the cells can be fluidically seeded onto culture surfaces in the bioreactor for seeding attachment, differentiation, and growth. In some configurations, the bioreactors can include scaffold surfaces upon which the cells can adhere and grow. In some configurations, the bioreactors can include horizontal, planar growth surfaces. A first cell type can be placed upon a first surface, the first surface can be covered with media from the vessels, and the cells can grow and differentiate. At a pre-selected or dynamically-determined, time, the first surface can be rotated so that a second cell type can be introduced onto a second surface. As the cells grow, features within the bioreactors can encourage the cells from both surfaces to intertwine, thus achieving the goal of incubating multiple cell types together.

Referring now to FIG. 1, system 2100 of the present teachings for manufacturing tissue can include, but is not limited to including, supervisor 2101 controlling stations along the production line. The stations can include, but are not limited to including, thaw subsystem 2147, expansion subsystem 2141, concentration subsystem 2143, and maturation subsystem 2145. Operationally, supervisor 2101 receives instructions from human-machine interface (HMI) 2133. The instructions can include parameter settings that can depend upon the type of cells being processed, and the type of tissue desired at the end of the process, for example. Supervisor 2101 can communicate with thaw subsystem 2147, receiving status messages and providing command messages. In some configurations, supervisor 2101 and thaw subsystem 2147 can be enabled, for example, but not limited to, by ROCKWELL AUTOMATION® COMPACTLOGIX® PLCs, and their communication can be conducted through, for example, but not limited to, an Ethernet connection. Supervisor 2101 can provide commands to thaw subsystem 2147, expansion subsystem 2141, concentration subsystem 2143, and maturation subsystem 2145, using, for example, but not limited to, the open platform unified architecture protocol (OPC UA) and/or the Ethernet protocol, and, in the case of expansion subsystem 2141, through network HMI 2103.

Continuing to refer to FIG. 1, supervisor 2101 can manage the operation of system 2100. Supervisor 2101 can track the states of the subsystems, user input, and sensor input, and can make pre-defined codes available to components of the system that can interpret the codes and act accordingly.

Figure 8:
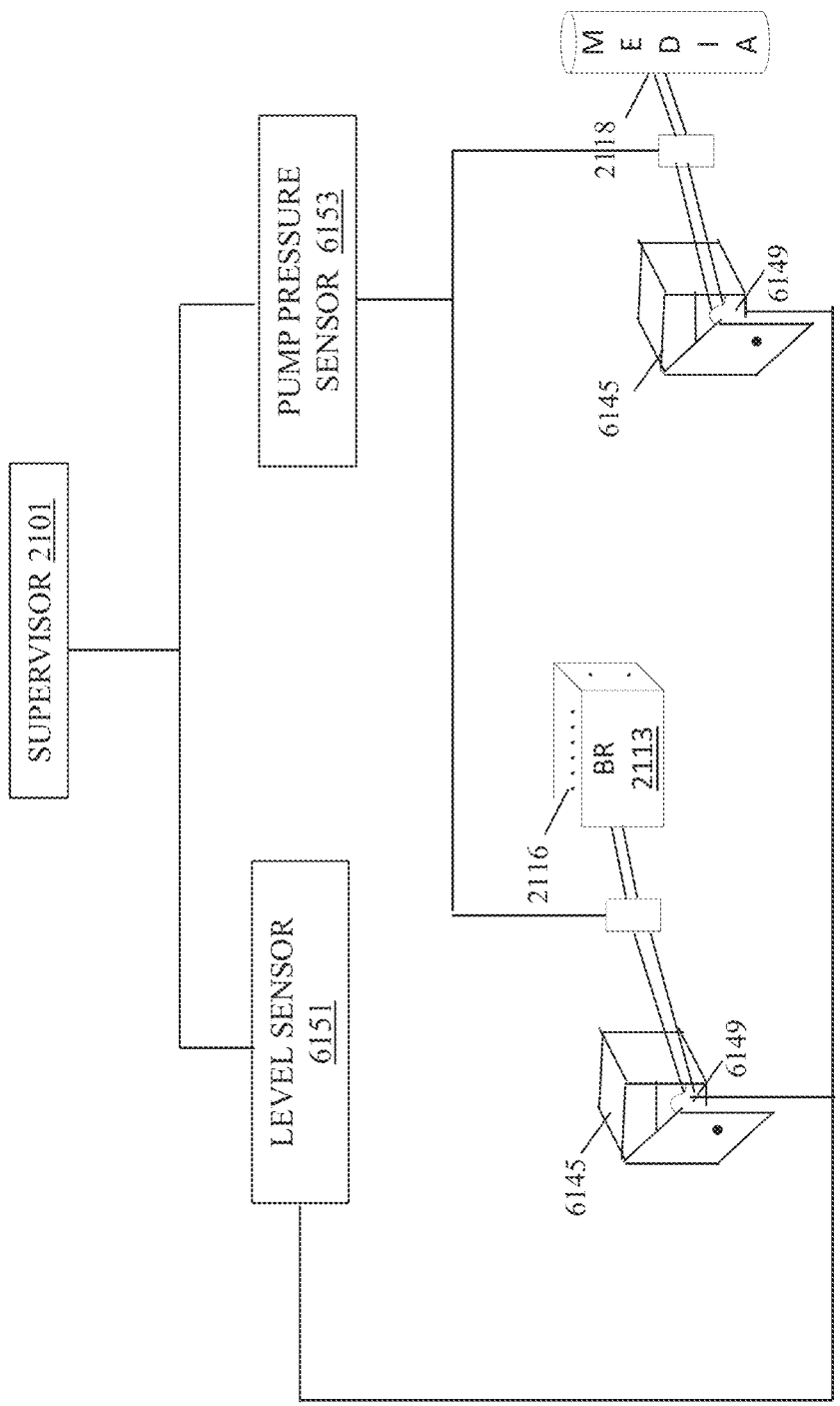
FIG. 8 is a schematic block diagram of the media supply subsystem under control of the supervisor of the present teachings.

Continuing to refer to FIG. 1, thaw subsystem 2147 can thaw cells in vial(s) 2163. After supervisor 2101 determines cells to be thawed, supervisor 2101 can initiate cell seeding from thaw subsystem 2147 to expansion subsystem 2141. Expansion subsystem 2141 can pump the thawed cells from vial 2163 to bioreactor vessel(s) 2113, and supervisor 2101 can enable media to be pumped into bioreactor vessel(s) 2113 from reservoir 6149 (FIG. 8). When the cells have reached a pre-selected density, expansion subsystem 2141 can perform tasks such as draining and washing, and can inform supervisor 2101 and can transfer the cells to concentration subsystem 2143 where the expanded cells can be concentrated. Supervisor 2101 can optionally accept user input at various points during these processes if desired or necessary. Supervisor 2101 can communicate with concentrator subsystem through a gateway that, in some configurations, can use, but is not limited to using, a Profinet protocol. Supervisor 2101 can monitor a concentration recipe, for example. The recipe can include a phase value that can be used to trigger a stop command to concentration subsystem 2143, and a message to expansion subsystem 2141 indicating that it can proceed to a subsequent step in the process. Supervisor 2101 can request status updates from concentrator subsystem 2143, and concentrator subsystem 2143 can send status commands to supervisor 2101. When the cell have reached the desired concentration, cells can return to expansion subsystem 2141, and supervisor 2101 can direct maturation subsystem 2145 to pump cells into bioreactor(s) 2114, and to pump conditioned media from vessel(s) 2118 into bioreactor(s) 2114. Media controller 2121 can condition the media in vessel(s) 2118 to prepare the media to properly nourish the cells in bioreactor 2114. In some configurations, bioreactor 2114 can include a shallow box having opposing interior sides. Incubator controller 2123 can control a positioning device to position bioreactor 2114 so that a first opposing interior side is facing the ground, and a second opposing side is facing the first opposing side. As cells are pumped into bioreactor(s) 2114, the cells can respond to gravity and tend to adhere to the second opposing side. Fresh media can be added to bioreactor 2114, critical process parameters can be monitored/adjusted, controlled washes can be performed, and media exchanges to support differentiation can be performed. Incubator controller 2123 can later seed the same or alternate cell types into bioreactor 2114. Bioreactor 2114 can be rotated prior to the second seeding to promote cell adherence on alternate surfaces. Additional rounds of seeding can be performed as such. Fluid lines from media 2118 to bioreactor 2114 can reside in a hollow spindle to maintain their integrity as bioreactor 2114 is flipped.

Continuing to refer to FIG. 1, maturation subsystem 2145 can include media controller 2121 and incubator controller 2123. Media controller 2121 can condition the media that will provide nutrition to the cells in bioreactor(s) 2114, controlling characteristics such as, for example, but not limited to, temperature, pH, and dissolved oxygen. Media conditioned to have the desired characteristics can flow through the cells adhering to either of upper or lower surfaces of shallow boxes within bioreactor 2114. Media controller 2121 can include, but is not limited to including, a LABOWL™ control system. Incubator controller 2123 can include, but is not limited to including, a ROCKWELL AUTOMATION® COMPACTLOGIX® PLC.

Continuing to refer to FIG. 1, supervisor 2101 can receive and process information sensed from the refrigerated media from load cells 2125 and pressure sensors 2127 using an Ethernet protocol. Processing can include using data from load cells 2125 to determine how much media remain in the media storage area. Supervisor 2101 can alert users, through process HMI 2133, about the need to replenish media. Supervisor 2101 can send and receive data to/from process HMI 2133 using an Ethernet protocol, for example. Messages initiated from thaw subsystem 2147, expansion subsystem 2141, concentration subsystem 2143, and maturation subsystem 2145 can be directed through supervisor 2101 to process HMI 2133. In some configurations, gateways can be used to enable communications between subsystems. Message acknowledgements can pass through the reverse path. Supervisor 2101 can communicate with remote server 2135 (FIG. 3) that can manage database 2131. Data from operational runs of the system of the present teachings can be stored, perhaps remotely, by logging processor 2129, if desired. Conventional means, such as, for example, but not limited to, ROCKWELL AUTOMATION® FACTORYTALK® Historian software, can be used to receive and catalog the data.

Figure 2A:
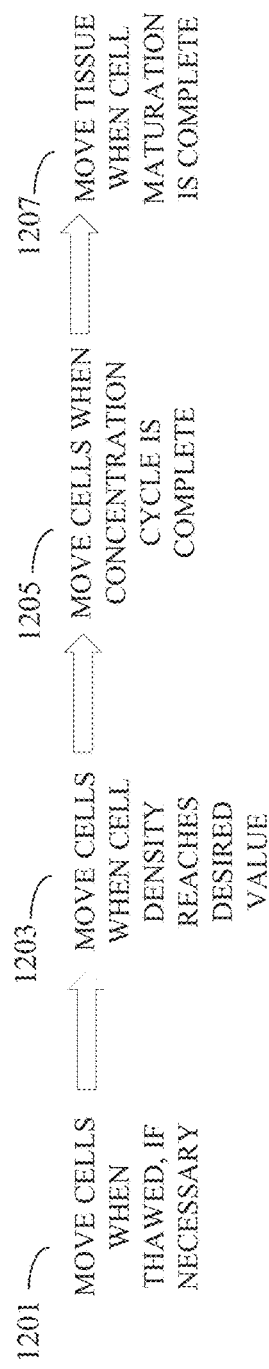
FIGS. 2A and 2B are flow diagrams of the process orchestrated by the supervisor of the system of the present teachings.

Referring now to FIGS. 1 and 2A, system 2100 (FIG. 1) can be used to create tissue from cells by including supervisor 2101 (FIG. 1) that can respond to triggers presented by each subsystem. For example, when supervisor 2101 (FIG. 1) detects that cells are thawed, system 2100 (FIG. 1) can include the step of moving 1201 (FIG. 2A) the thawed cells from thaw subsystem 2147 (FIG. 1) to expansion subsystem 2141 (FIG. 1). When expansion subsystem 4141 (FIG. 1) detects a desired density of cells, system 2100 (FIG. 1) can include the step of moving 1203 (FIG. 2A) cells from expansion subsystem 2141 (FIG. 1) to concentrator subsystem 2143 (FIG. 1). When supervisor 2101 (FIG. 1) detects that the desired cell concentration has been achieved, system 2100 (FIG. 1) can include the step of moving 1205 (FIG. 2A) cells from concentrator subsystem 2143 (FIG. 1) to expansion subsystem 2141 (FIG. 1), and when cells have reached a desired maturity, which may be determined by the expiration of a pre-selected amount of time, system 2100 (FIG. 1) can include the step of enabling moving 1207 (FIG. 2A) the matured tissue out of maturation subsystem 2145 (FIG. 1). In some configurations, expansion subsystem 2141 (FIG. 1) can start the process enabled by system 2100 (FIG. 1) by sending messages to process HMI 2133 (FIG. 1) through supervisor 2101 (FIG. 1), thereby prompting a user for input. Supervisor 2101 (FIG. 1) can process user inputs, exchange messages with expansion subsystem 2141 (FIG. 1) to enable flow control, and direct thaw subsystem 2147 (FIG. 1) to (1) check for vials 2163 (FIG. 1), (2) check the position of needles that can be situated to puncture vials 2163 (FIG. 1) as described elsewhere herein, (3) determine if one of the needles has punctured the vial(s) 2163 (FIG. 1), and (4) check if there are no more vials 2163 (FIG. 1) to process, and then provide the status of these checks to expansion subsystem 2141 (FIG. 1). In some configurations, needle position can be assumed and checking can be reduced. In some configurations, vials 2163 (FIG. 1) can be decapped, and contents can be withdrawn in various ways, including, but not limited to, inserting mounted needles into the decapped mouths of vials 2163 (FIG. 1). In response, expansion subsystem 2141 (FIG. 1) can message supervisor 2101 (FIG. 1). In some configurations, supervisor 2101 (FIG. 1) can inform thaw subsystem 2147 (FIG. 1) that a flush of vial(s) 2163 (FIG. 1) is in progress, or that the flush is complete. In some configurations, the following protocol can be executed between supervisor 2101 (FIG. 1) and expansion subsystem 2141 (FIG. 1): (1) expansion subsystem 2141 (FIG. 1) can message supervisor 2101 (FIG. 1) to start thaw subsystem 2147 (FIG. 1), (2) supervisor 2101 (FIG. 1) can message expansion subsystem 2141 (FIG. 1) when vial 2163 (FIG. 1) is punctured, (3) expansion subsystem 2141 (FIG. 1) can message supervisor 2101 (FIG. 1) to set pre-selected valve states, (4) expansion subsystem 2141 (FIG. 1) can pump a pre-selected amount of fluid, (5) expansion subsystem 2141 (FIG. 1) can message supervisor 2101 (FIG. 1) when pumping is complete, (6) supervisor 2101 (FIG. 1) can message expansion subsystem 2141 (FIG. 1) when the gas purge is complete, and if there are more vials to process, and (7) expansion subsystem 2141 (FIG. 1) can message supervisor 2101 (FIG. 1) to set another pre-selected valve state based on whether or not there are more vials left to process. At this point, supervisor 2101 (FIG. 1) can message expansion subsystem 2141 (FIG. 1) to start the cell expansion process. When expansion subsystem 2141 (FIG. 1) determines that expansion is complete, expansion subsystem 2141 (FIG. 1) can message supervisor 2101 (FIG. 1), and supervisor 2101 (FIG. 1) can optionally message process HMI 2133 (FIG. 1) to prompt the user for further instructions, if necessary. Supervisor 2101 (FIG. 1) can message concentrator subsystem 2143 (FIG. 1) to begin the steps of the recipe, and concentrator subsystem 2143 (FIG. 1) can execute the recipe steps. When the recipe steps have completed, supervisor 2101 (FIG. 1) can message expansion subsystem 141 to re-suspend the cells to get the cells back into solution. At this point, supervisor 2101 (FIG. 1) can message maturation subsystem 2145 (FIG. 1) to seed cells in bioreactor 2114 (FIG. 1). Seeding can occur multiple times if desired.

Figure 2B:
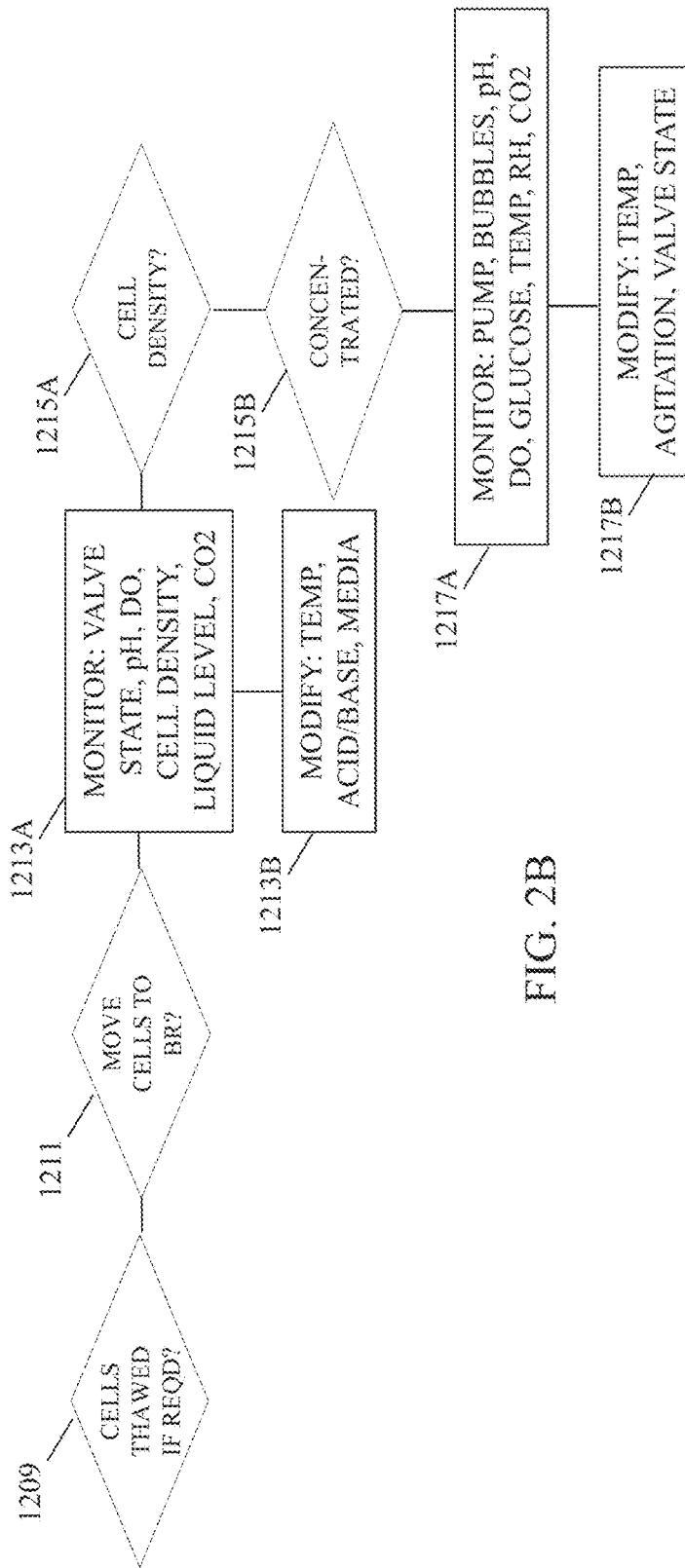

Referring now to FIGS. 2A and 2B, triggers to move from one step to another, and when one subsystem takes control from another, under control of supervisor 2101 (FIG. 1) can follow general guidelines, with variations possibly occurring within each subsystem depending upon the desired outcome. For example, if 1209 (FIG. 2B) cells are thawed, supervisor 2101 (FIG. 1) can enable moving 1201 (FIG. 1) the thawed cells into expansion subsystem 2141 (FIG. 1). In some configurations, the tube(s) connecting thaw subsystem 2147 (FIG. 1) with expansion subsystem 2141 (FIG. 1) can include a means for detecting bubbles in the tube(s). When 1211 (FIG. 2B) bubbles are detected, supervisor 2101 (FIG. 1) can message expansion subsystem 2141 (FIG. 1) that priming is complete. In some configurations, the amount of pumping necessary to move the cells to expansion subsystem 2141 (FIG. 1) can be pre-determined, and when the pre-determined amount of pumping takes place, supervisor 2101 (FIG. 1) can message expansion subsystem 2141 to disable the flow of cells from thaw subsystem 2147 (FIG. 1). When the cells are in expansion subsystem 2141, various parameters can be monitored 1213A (FIG. 2B), and certain things can be adjusted 1213B (FIG. 2B), possibly based on the monitored values. Supervisor 2101 can monitor, for example, but not limited to, valve state of the fluid valves that are controlling the flow of fluid through expansion subsystem 2141 (FIG. 1). Expansion subsystem 2141 (FIG. 1) can also monitor characteristics of fluid flowing around the cells such as, for example, but not limited to, fluid level in a media vessel 2118 (FIG. 1), fluid temperature, fluid pH, dissolved oxygen in the fluid, agitation rate, and media conductivity. These characteristics can be adjusted in various ways. For example, carbon dioxide can be added to the liquid to adjust the pH, oxygen or nitrogen can be added to the liquid to adjust the dissolved oxygen, and liquid can be added or removed from a reservoir to adjust the liquid level and to adjust the characteristics of the liquid. Cell density can also be monitored. When 1215A (FIG. 2B) cell density reaches a pre-determined amount, supervisor 2101 (FIG. 1) can enable moving the cells to concentrator subsystem 2143 (FIG. 1). When 1215B (FIG. 2B) a desired cell concentration is reached, supervisor 2101 (FIG. 1) can enable moving the cells to maturation subsystem 2145 (FIG. 1). Maturation subsystem 2145 (FIG. 1) can monitor 1217A (FIG. 2B) and adjust 1217B (FIG. 2B) the media to adjust the environment of the cells. Monitoring the media in vessel 2118 (FIG. 1) can include monitoring characteristics such as, for example, but not limited to pH, dissolved oxygen, temperature, and agitation. Monitoring the media in tubing connecting bioreactors and media storage can include in-line monitoring of characteristics such as, for example, but not limited to pH, glucose, dissolved oxygen, and air bubbles. Monitoring the media in the incubator housing bioreactor(s) 2114 can include monitoring characteristics such as, for example, but not limited to carbon dioxide, temperature, and relative humidity. The status of the pumping system and the leading edge of bubbles in the tubing between vessel(s) 2118 and bioreactor(s) 2114 can be monitored. The temperature of the media can be adjusted, and the media can be agitated. Other action can be taken and/or alerts can be generated based on the values of monitored characteristics and equipment.

Figure 3:
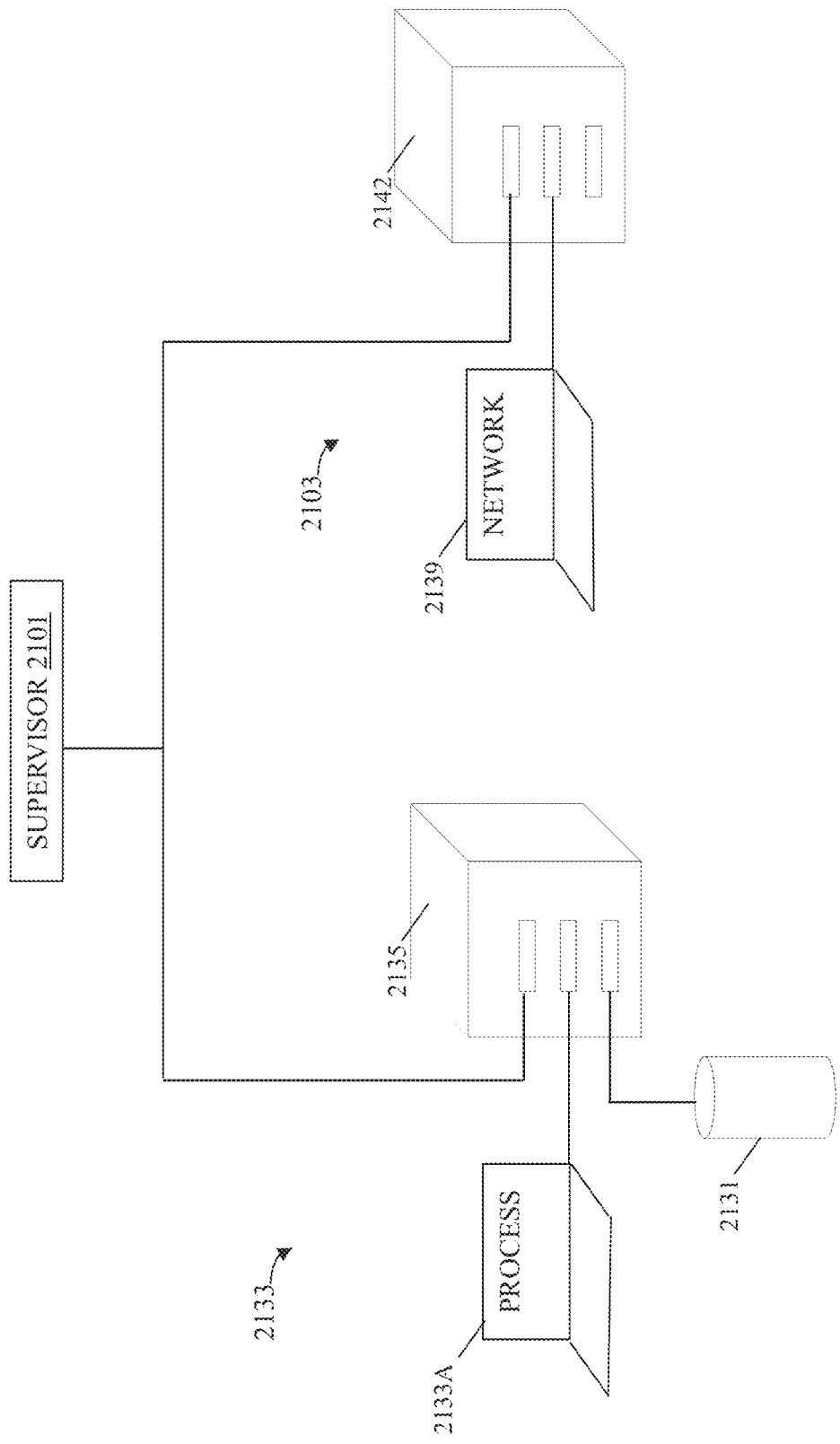
FIG. 3 is a schematic block diagram of the human-machine interface under control of the supervisor of the present teachings.

Referring now to FIG. 3, user input into system 2100 (FIG. 1) can be provided with respect to process control 2133 and network control 2103. In some configurations, input with respect to process parameters and input with respect to network parameters can be provided and processed at a single computer. In some configurations, multiple monitors—process HMI monitor 2133A and network HMI monitor 2139—and/or processors—process computer 2135 and network computer 2139—can receive and process user input, provide that input to supervisor 2101, and receive messages including commands, status, and data from supervisor 2101. In some configurations, each of expansion subsystem 2141, concentration subsystem 2143, maturation subsystem 2145, and the incubator can include an HMI. In some configurations, user interaction with expansion subsystem 2141 can initiate the tissue generation process. In some configurations, users can change recipes and setpoints by interacting with the HMIs of concentration subsystem 2143, incubator, and maturation subsystem 2145. In some configurations, process computer 1135 can host logging processor 2129 (FIG. 1) that can collect time series information and store it in, for example, database 1231 (FIG. 1). Database 2131 (FIG. 1) can include physical long-term storage, cloud storage, short-term storage, or any other way to store data electronically. System 2100 (FIG. 1) can be controlled remotely through user input into a wireless device such as, for example, but not limited to, a cell phone or a tablet, or locally through monitors co-located with the physical hardware of system 2100 (FIG. 1).

Figure 4:
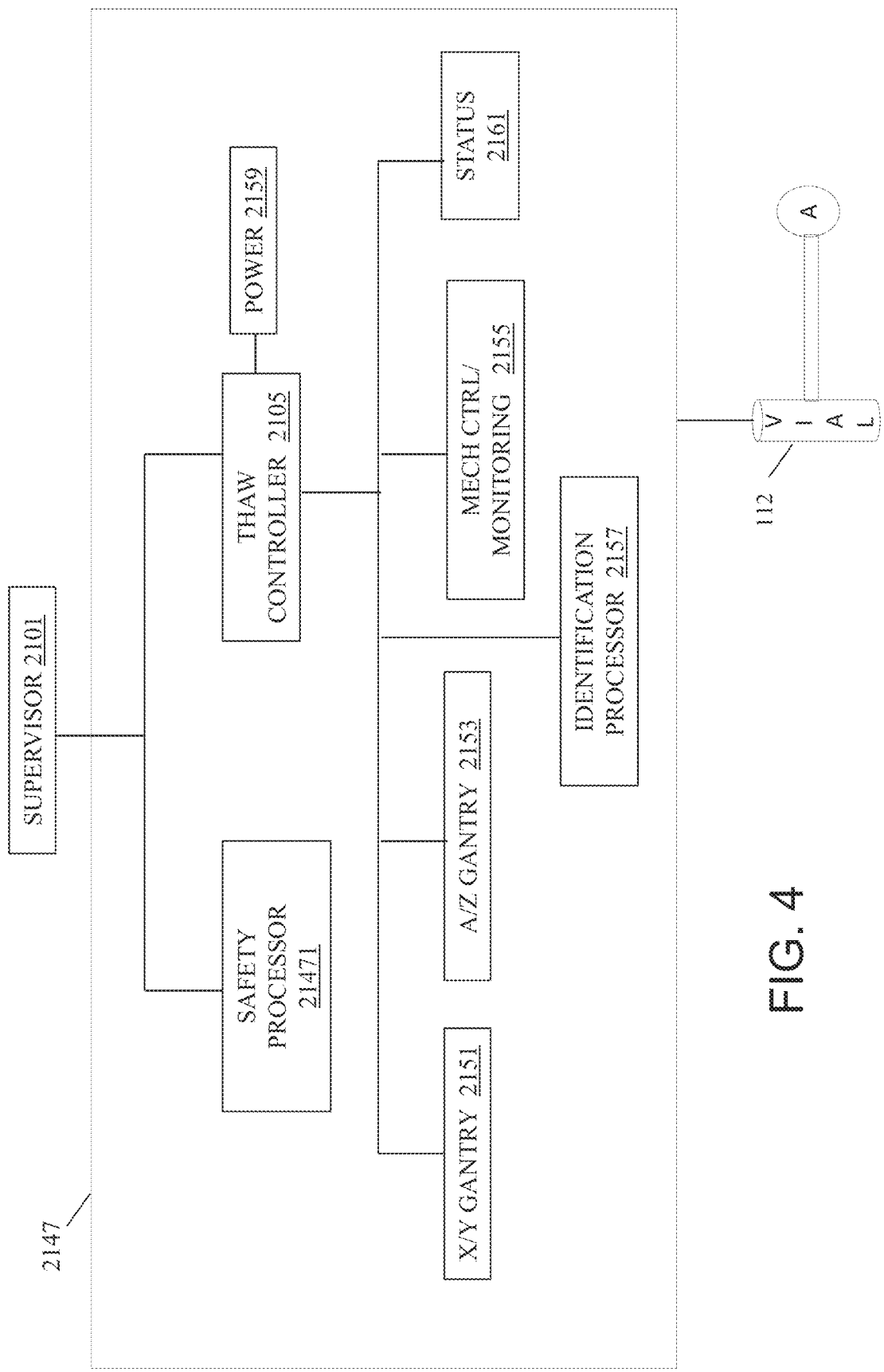
FIG. 4 is a schematic block diagram of the thaw subsystem under control of the supervisor of the present teachings.

Referring now to FIG. 4, thaw subsystem 2147 can receive vials of frozen cells and safely and efficiently achieve uniform thawing of the cells as described elsewhere herein. Supervisor 2101 can coordinate the activities of thaw subsystem 2147 with the activities of the other subsystems. For example, supervisor 2101 can receive recipe information and emergency stop information from HMI subsystems 2133/2103 (FIG. 3), and can supply that information to components of thaw subsystem 2147. Safety processor 21471 can monitor the status of safety equipment associated with thaw subsystem 2147, and provide that information to supervisor 2101. Supervisor 2101 can message the status information to HMI subsystems 2133/2103 (FIG. 3) for possible display to a user. The user can possibly initiate an emergency stop based on the safety equipment status. In some configurations, safety processor 21471 can receive an emergency stop message from supervisor 2101 and can initiate shutting down activities associated with thaw subsystem 2147 such as, for example, gantry, and therefore the movement of vial 2163. Reasons for unplanned stoppage can include, but are not limited to including, vial misplacement, vial defect, gantry malfunction, or unknown vial barcode.

Continuing to refer to FIG. 4, thaw subsystem 2147 can enable accessing vial(s) 2163, accessing an identifier associated with vial(s) 2163, moving vial(s) 2163 from one station to another, and receiving status information from the processors and controllers manipulating vial(s) 2163. Mechanical control/monitoring 2155 can enable choosing a vial from a vial bank by controlling jaws that perform pick and place of the vial. Identification process 2157 can access an identification associated with vial 2163. In some configurations, the identification can include a barcode, and the identification process 2157 can include a barcode reader. Identification process 2157 can provide the vial identifier to supervisor 2101, and the vial identification can be used to determine processing parameters associated with the vial. In some configurations, the processing parameters can be in the form of a recipe for processing of the cells within the vial. Supervisor 2101 and the subsystems can use the recipe to automate processing of the cells. The recipe can be at least partly formulated by, for example, a user using the HMI subsystems.

Continuing to refer to FIG. 4, gantry controllers—X/Y gantry controller 2151 and A/Z gantry controller 2153—can enable the vial to move from station to station along a vial rail. In some configurations, a stepper motor controller module such as, for example, but not limited to, a FESTO® CMXH-ST2 controller, can control X/Y axis motors. In some configurations, field bus modules such as, for example, but not limited to, FESTO® bus node CTEU-EP can provide an interface between the A/Z axis motors and thaw controller 21491. The gantry controllers can provide gantry positions and gantry status to thaw controller 21491. Status processor 2161 can monitor other components of thaw subsystem 2147 and report that information to thaw controller 21491. Thaw controller 21491 can enable power to thaw subsystem components through power controller 2159, which can supply power status to thaw controller 21491. Thaw controller 21491 can exchange information with the vial rail, pick and place equipment, jaw valves, pressure switches, and refrigerator alarms through a manifold such as, for example, but not limited to, a FESTO® manifold.

Figure 4A:
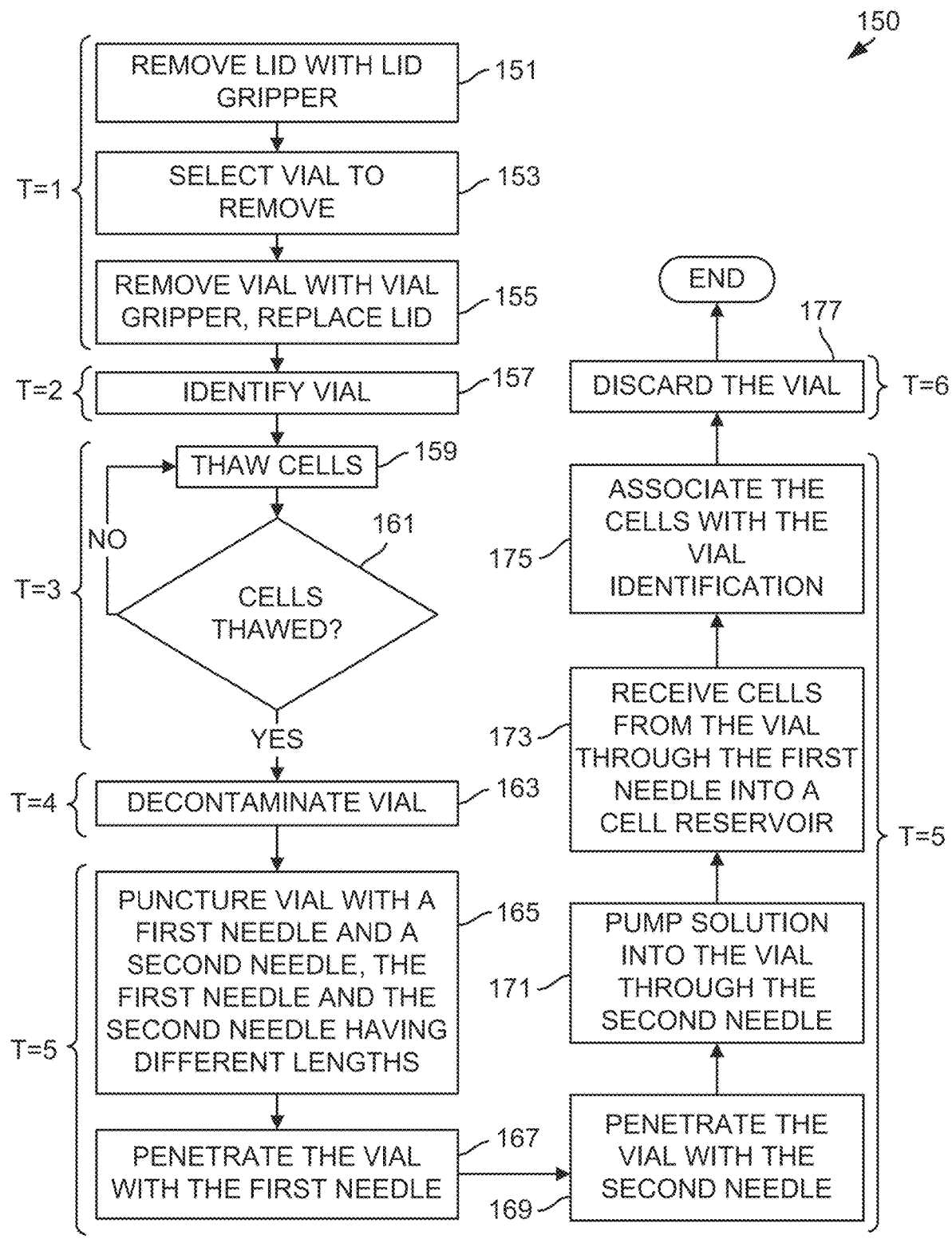
FIG. 4A is a flowchart of the method of the present teachings.

Referring now to FIG. 4A, method 150 of the present teachings for preparing cells for engineering tissue can generally include, but is not limited to including, thawing vials of cells, decontaminating the thawed vials, puncturing the decontaminated thawed vials, and removing the cells from the vials, the removal taking place in a controlled, clean volume surrounding the puncture station. These processes can be automatically initiated, enabling method 150 to be of use in a manufacturing line. Specifically, method 150 can include automatically removing 151 the lid of an insulated container station with a lid gripper. All automatic operations can be controlled by a thaw controller. Method 150 can include automatically selecting 153 a vial to remove from the insulated container. Vial selection can be based on a pre-selected vial location, or sensors can determine vial positions and positions where vials have been removed. The sensors can inform the thaw controller to locate the lid gripper in a location that includes a vial. Method 150 can include automatically removing 155 the vial from the insulated container using a vial gripper, and replacing the insulated container lid using the lid gripper. Both grippers can be controlled by the thaw controller. Method 150 can optionally include automatically identifying 157 the vial. Identification can be enabled by, for example, but not limited to, an RFID device, bar code reader, or other type of sensor that can read a labeled vial or interrogate the contents of the vial. Method 150 can include automatically moving the vial to a thaw station and automatically thawing 159 the cells. The thaw station can include a thaw manager that, under control of and in communication with, the thaw controller, can indicate electronically when the cells are thawed. If 161 the cells are not determined, by the thaw manager and the thaw controller, to be in a thawed state, method 150 can include continuing to thaw 159 cells. If 161 the cells are determined to be thawed, method 150 can include automatically moving the vial to a decontamination station and decontaminating 163 the vial. Decontamination can include, but is not limited to including, automatically applying a substance such as alcohol to the exterior surface of the vial for a pre-determined amount of time. Method 150 can include automatically moving the vial into a controlled, clean volume surrounding the puncture station within an enclosure or hood when the thaw controller determines that decontamination is complete. Method 150 can include automatically puncturing 165 the vial with two needles when the vial is correctly positioned in a puncture station, where the needles are of different lengths. Method 150 can include penetrating 167 the vial up to a first pre-selected amount with a first of the two needles, and penetrating 169 the vial up to a second pre-selected amount with a second of the two needles. Different needle lengths of the two needles can ensure that the tips of the needles will extend to different levels within the vial. Method 150 can include automatically pumping 171 a solution into the vial through one of the needles, such as, for example, the second needle, when the thaw controller determines that the needles are properly positioned within the vial. In some configurations, the first needle can be shorter than the second needle. In some configurations, the needles can include beveled edges that can be clocked with the beveled edges pointing in opposite directions. Method 150 can include receiving 173 cells into the first needle as the cells are moved towards the first needle by the introduction of solution into the vial through the second needle. The cells can continue on their journey through tubing that can connect the first needle to a cell reservoir until a substantial number of cells have been evacuated from the vial. Method 150 can include automatically associating 175 the identified vial with the cells in the cell reservoir. Method 150 can optionally include pumping the solution for a pre-selected amount of time, automatically determining that the vial is empty of cells, automatically moving the vial outside of the hooded area, and/or automatically retrieving the vial with the vial gripper. Method 150 can include automatically discarding 177 the vial into a waste container using the vial gripper under the control of the thaw controller.

Figure 4B:
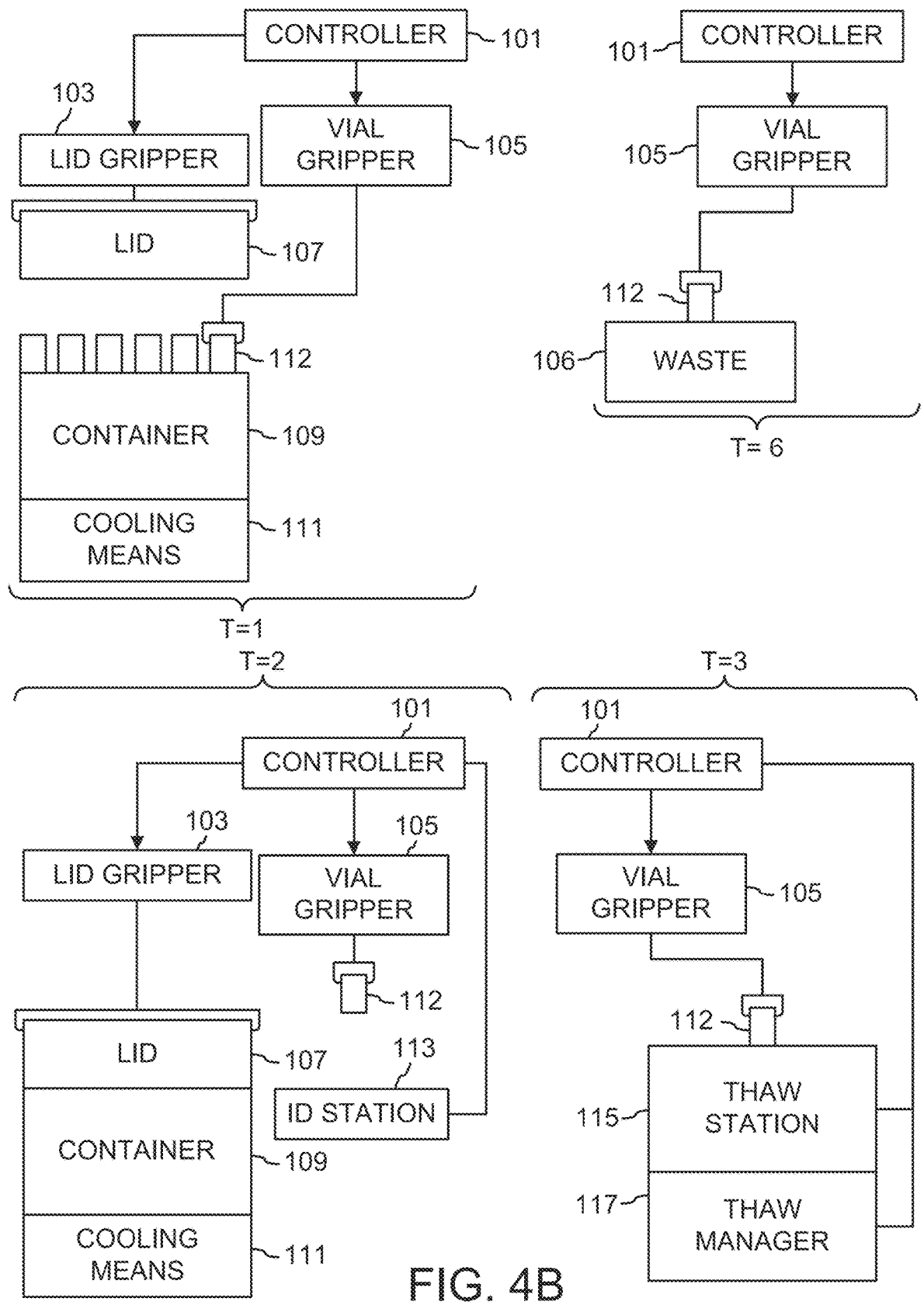
FIGS. 4B and 4C are schematic block diagrams of an exemplary time progression of the method of the present teachings.

Referring to FIG. 4B, the process of cell preparation of the present teachings is described herein in terms of a temporally-related sequence of events. Other designs are possible, for example, multiple vials 112 can be processed approximately simultaneously, or processing of multiple vials 112 can overlap, or various steps in the process can be overlapped where possible, or processing timing can include timeframes that vary from one vial to another based, for example, on changing processing conditions. For example, lid gripper 103 can replace lid 107 at the same time as vial gripper moves vial 112 from identification station 113 (when present) to thaw station 115. A configuration that involves sequential temporally-based processing can include, at time T=1, thaw controller 101 can instruct lid gripper 103 to lift lid 107 from insulated container 109 whose temperature can be maintained by cooling means 111. Under lid 107 can sit frozen vials 112. Thaw controller 101 can instruct vial gripper 105 to retrieve vial 112 from insulated container 109. At time T=2, thaw controller 101 can instruct lid gripper to replace lid 107 on insulated container 109. In some configurations, thaw controller 101 can instruct vial gripper 105 to move vial 112 past identification station 113 (when present), and can receive vial identification information from identification station 113 (when present). Other methods of creating a record of the identification of vial 112 can be used such as, for example, but not limited to, reading identifying information from insulated container 109, or associating the cells in vial 112 with vial 112 later in the cell preparation process of the present teachings. At time T=3, thaw controller 101 can instruct vial gripper 105 to move vial 112 from its previous location to thaw station 115. At thaw station 115, thaw station controller 117 can signal to thaw controller 101 when the cells in vial 112 are deemed to be thawed according to the process executed by thaw station 115.

Figure 4C:
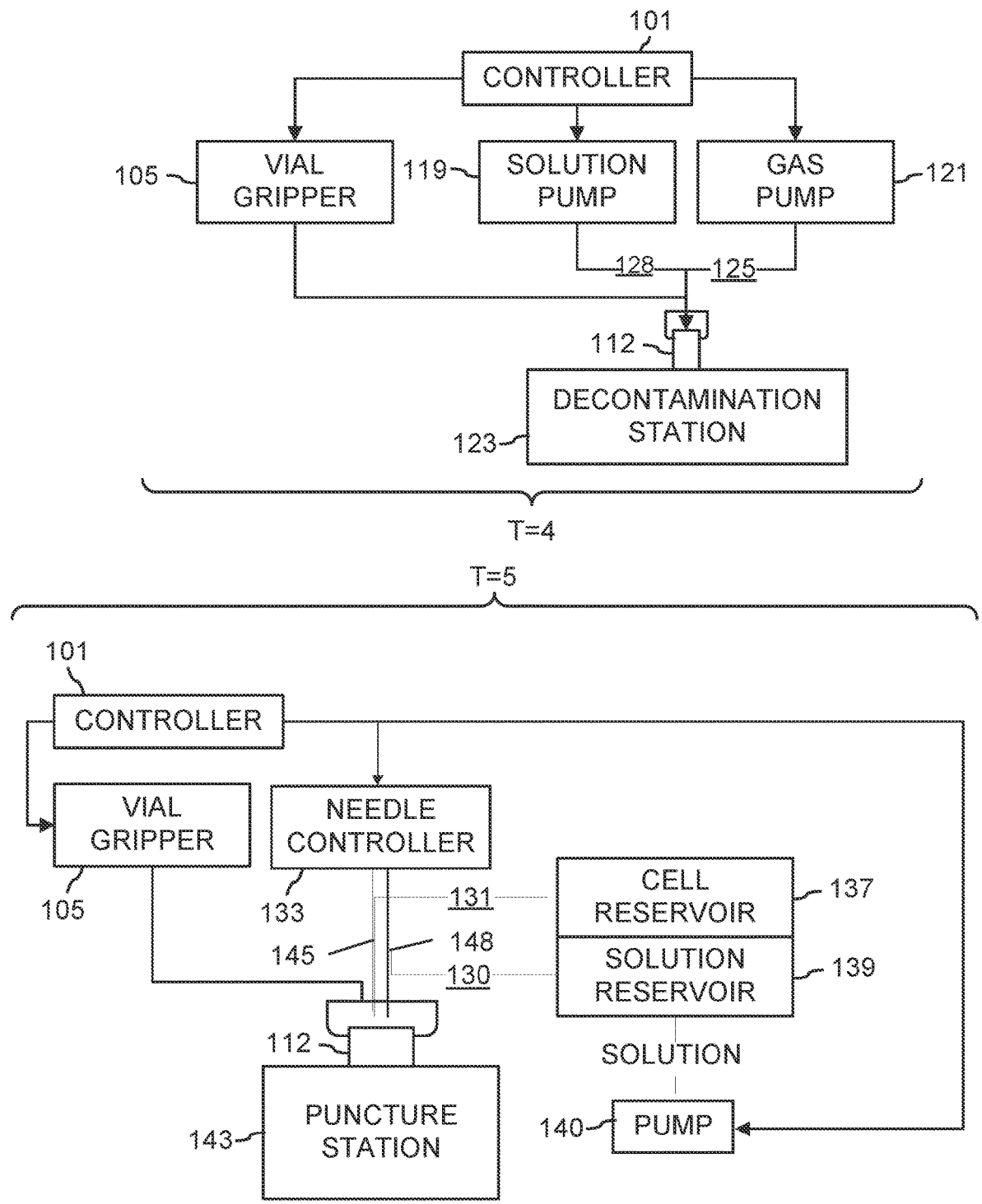

Referring now to FIG. 4C, at time T=4, thaw controller 101 can instruct vial gripper 105 to move vial 112 from its previous location to decontamination station 123. When thaw controller 101 determines that vial 112 is correctly positioned in decontamination station 123, thaw controller 101 can instruct solution pump 119 to provide a decontamination solution through tube 128 toward the exterior of vial 112. In some configurations, the decontamination solution can include antibacterial and volatile characteristics, for example. Thaw controller 101 can, according to a pre-selected recipe or according to sensor-related stimuli, pump a gaseous substance toward vial 112. The gaseous substance can include air, or another mixture of gases appropriate for the decontamination process. At T=5, thaw controller 101 can instruct vial gripper 105 to move vial 112 through flaps 127 (FIG. 4D) under hood 124 and into puncture station 143. When thaw controller 101 determines that vial 112 is appropriately positioned with respect to guided actuator 207 (FIG. 4H) and needles 145/148, thaw controller 101 can instruct needle controller 133 to lower guided actuator 207 (FIG. 4H) so that needles 145/148 can puncture vial 112. When needles 145/148 are positioned according to a pre-selected location or a sensor-based location, thaw controller 101 can instruct solution pump 140 to pump solution from solution reservoir 139 through tubing 130 and needle 148 into vial 112. As cells in vial 112 are displaced by the solution, the cells can find their way into needle 145 and out through tubing 131 to cell reservoir 137. At T=6 (FIG. 4B), thaw controller 101 can determine, by a pre-selected method or by a sensor-based calculation, that enough cells have been displaced from vial 112 into cell reservoir 137, and can instruct vial gripper 105 to remove vial 112 from puncture station 143 and place it into waste station 106 (FIG. 4B). Thaw controller 101 can associate cells in cell reservoir 137 with vial 112 in a way that can depend upon the method of identifying vial 112 as described herein.

Figure 4D:
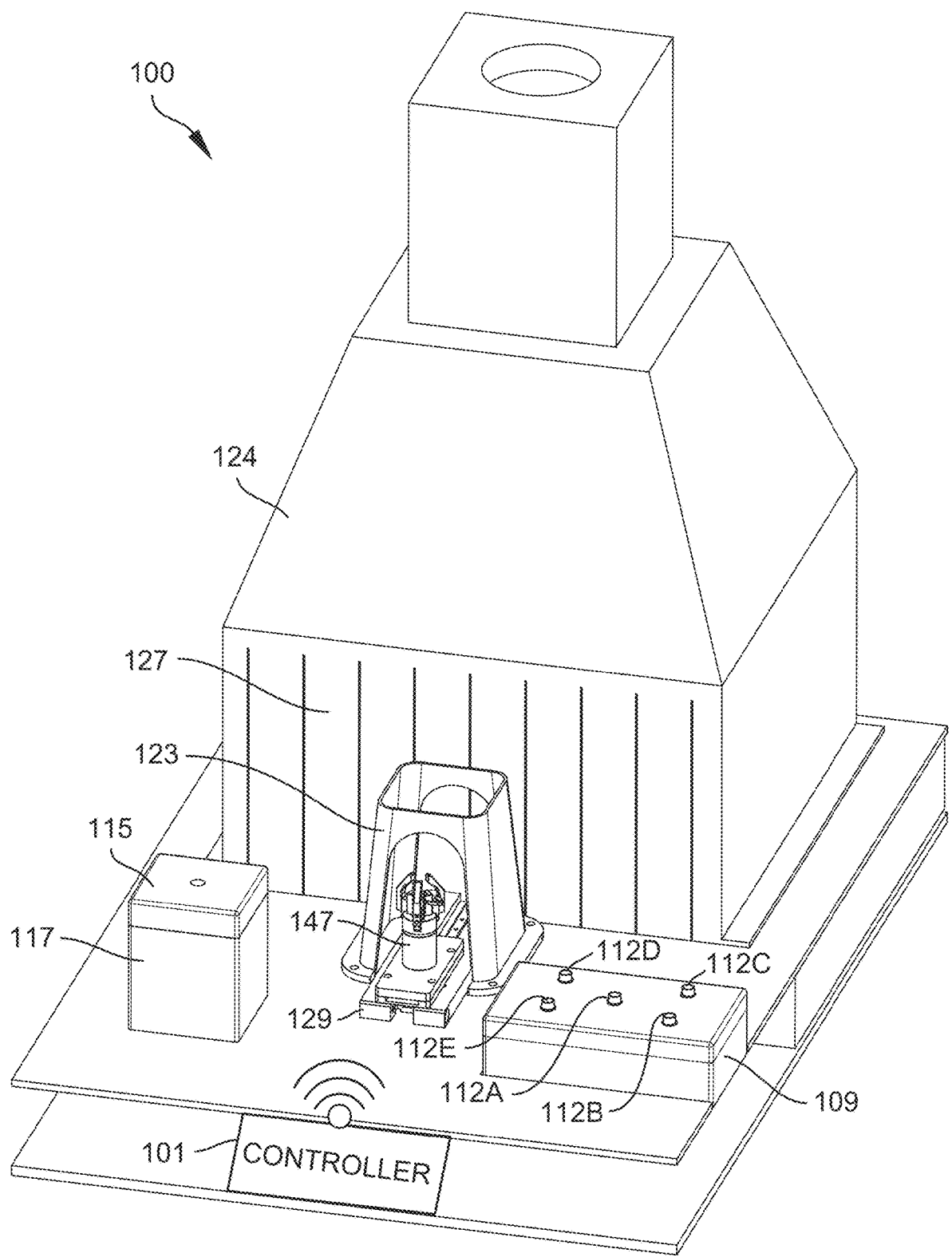
FIG. 4D is a perspective diagram of the system of the present teachings.
Figure 4E:
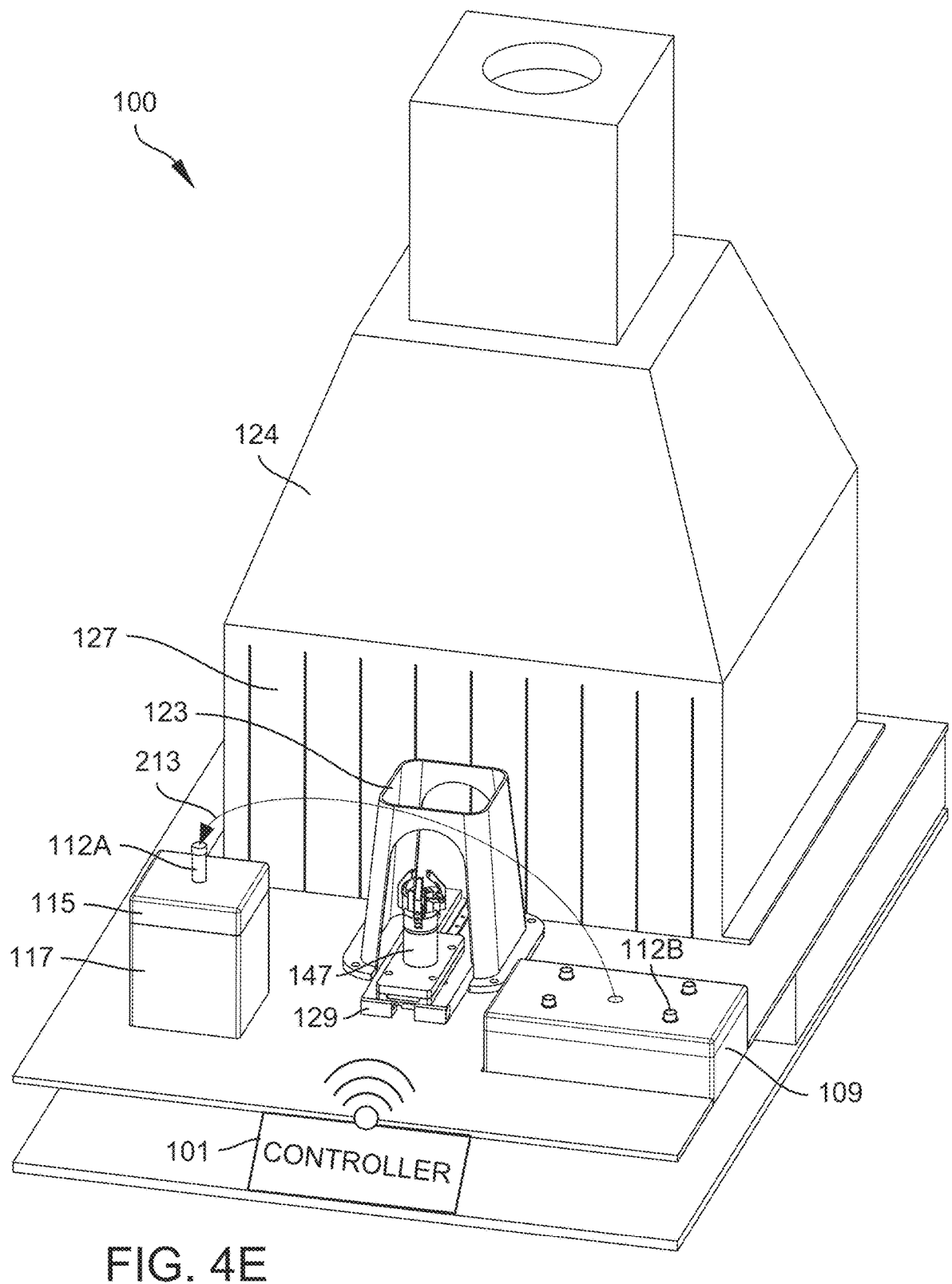
FIGS. 4E and 4F are perspective diagrams of the system of FIG. 4D showing the vial movement of the present teachings.
Figure 4F:
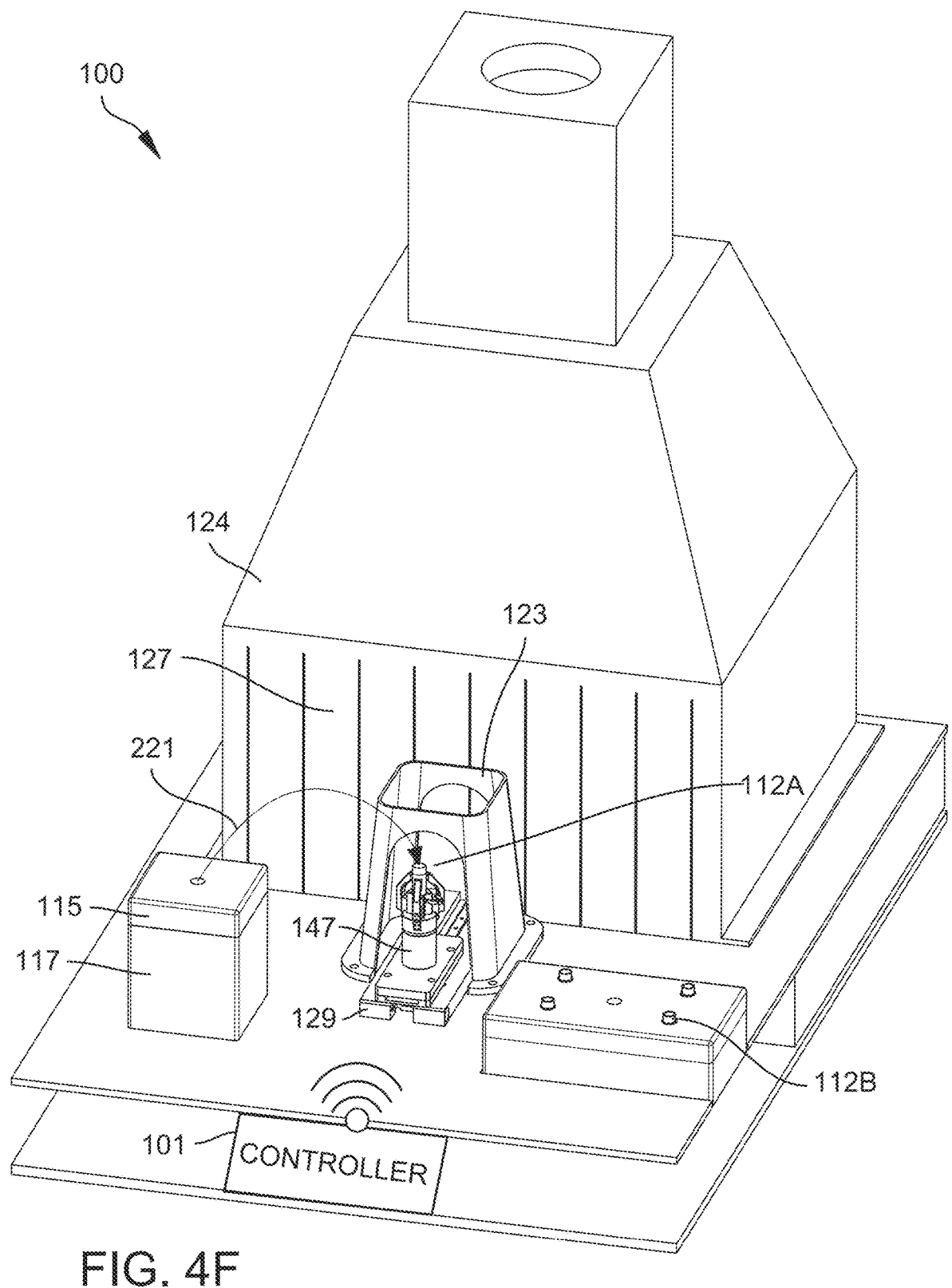

Referring now to FIGS. 4D-4F, automated system 100 for performing method 150 (FIG. 4A) can include insulated container 109 that can maintain the integrity of the frozen cells. Insulated container 109 can include mount locations for any number of vials 112A-112E. Insulated container 109 can include any commercial cell insulated container station that can accommodate the maintaining frozen cells at a pre-determined temperature. In some configurations, insulated container 109 can include a material that can passively maintain the contents of insulated container 109, for example, the cells, approximately within a pre-determined temperature range. The pre-determined temperature range can be based on the requirements of the contents and their subsequent processing. In some configurations, insulated container 109 can include an active system for maintaining the contents at approximately within a pre-determined temperature range. The active system can include a freezer, and can the temperature in the freezer can be controlled by controller 101. Controller 101 can include wired or wireless communications with the systems that are being controlled, and can manage the sequencing of events as set out herein. System 100 can include a moving means to move vials 112A-112E, for example, but not limited to, one-by-one into thaw station 115. The moving means can be controlled by controller 101. Thaw station 115 can include, but is not limited to including, a commercially-available thaw station that can accommodate thaw requirements described herein, for example, rapid thawing with high reproducibility and minimal risk of contamination. Thaw station 115 can include, for example, but not limited to, Astero Bio's Thaw-STAR® Automated Cell Thawing system that can be controlled by controller 101 through a custom interface.

Continuing to refer to FIGS. 4D-4F, in some configurations, thaw controller 101 can manage an apparatus (not shown) that can move vial 112A, for example, from insulated container 109 to thaw station 115 along path 213, for example. The moving apparatus can include a mechanism for grasping and freeing vial 112A, for example, by means of controlled suction, controlled clamps, controlled grips, or any other suitable means. Thaw controller 101 can include communicating control information with a control interface to thaw station controller 117, vial transport means 129, and gripping systems, as well as a decontamination means (not shown) associated with decontamination station 123, puncture station 143 (FIG. 4J), and, optionally, insulated container 109. Thaw station controller 117 can provide an interface between thaw controller 101 and thaw station 115.

Continuing to refer to FIGS. 4D-4F, vial gripper system 147 can include, but is not limited to including, commercially-available vial grippers such as, for example, but not limited to, FESTO® three-point grippers, or any gripper that can include a similar gripping force. Vial gripper system 147 can be mounted upon plate 211 that can enable mounting to, for example, but not limited to, movement means 129. Movement means 129 can include, but is not limited to including, a commercially-available movement assembly that can move vial gripper system 147 from decontamination station 123 to puncture station 143 (FIG. 4J).

Figure 4G:
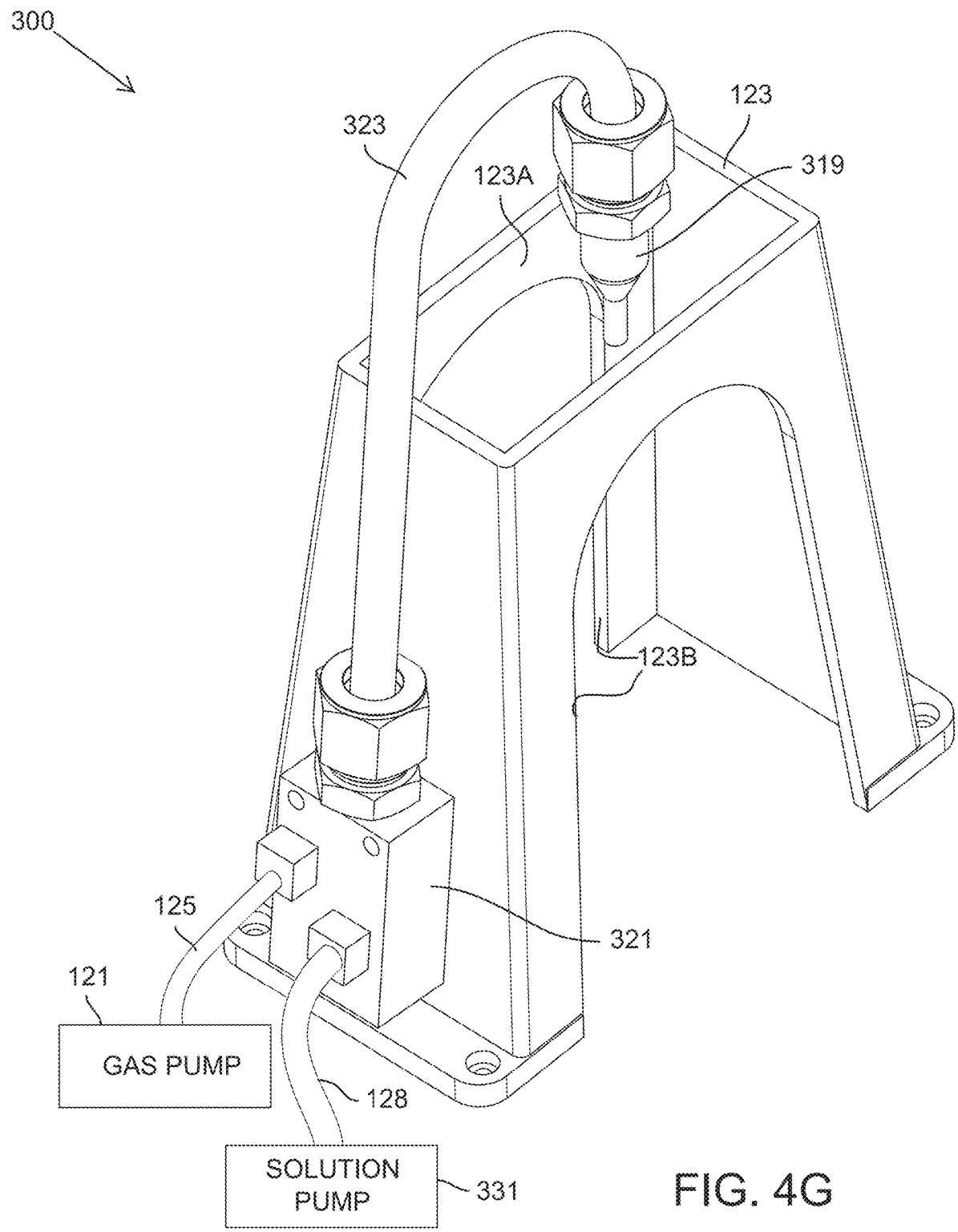
FIG. 4G is a perspective diagram of the decontamination station of the present teachings.

Continuing to refer to FIGS. 4D-4F, thaw station controller 117 can include electronics to sense the state of the contents of vial 112A, for example, and to inform thaw controller 101 when the time has come to move vial 112A, for example, to vial gripper system 147. The moving apparatus can include attaching vial 112A, for example, by means described herein, and moving vial 112A, for example, from thaw station 115 to vial gripper system 147 along 13 221, for example. Thaw controller 101 can recognize when vial 112A, for example, is correctly positioned in vial gripper system 147, and can control tightening of grips 149 (FIG. 4H) around vial 112A, for example. When grips 149 are sensed to be tightened a pre-selected amount, thaw controller 101 can instruct movement means 129 to move vial gripper system 147 and vial 112A, for example, into decontamination station 123 that can decontaminate the exterior of vial 112A. In some configurations, decontamination means 300 (FIG. 4G) can include sprayer 319 (FIG. 4G), depositing material from gas tube 125 (FIG. 4G) and/or solution tube 128 (FIG. 4G) onto vial 112A. The material can be pumped through decontamination tube 323 (FIG. 4G), and through cavity 123A (FIG. 4G) onto vial 112A. Misting manifold 321 (FIG. 4G) can assist in individual control of gas tube 125 (FIG. 4G) and solution tube 128 (FIG. 4G) as gas pump 121 (FIG. 4G) and solution pump 331 (FIG. 4G) pump gas and solution into decontamination tube 323 (FIG. 4G). Doorways 123B (FIG. 4G) can optionally include doors that can retain the solution within decontamination station 123. The doors can optionally include, but are not limited to including, flaps and/or bristles. Decontamination means 300 (FIG. 4G) can be controlled, and its activation time can be sequenced, by thaw controller 101. Decontamination means 300 (FIG. 4G) can decontaminate the exterior of vial 112A before it enters through, for example, flaps 127, the controlled, clean volume surrounding the puncture station environment within hood 124. In some configurations, hood 124 can include a device that can accommodate laminar air flow forced, for example, by positive pressure, through an air filter that can, for example, filter particles down to about between 0.12 and 0.3 microns in size. In some configurations, the filtered air can exit through the work area of hood 124. In some configurations, hood 124 can include, for example, an ISO Class 5 cleanroom that has at most $10^5=100,000$ particles/cubic meter.

Figure 4H:
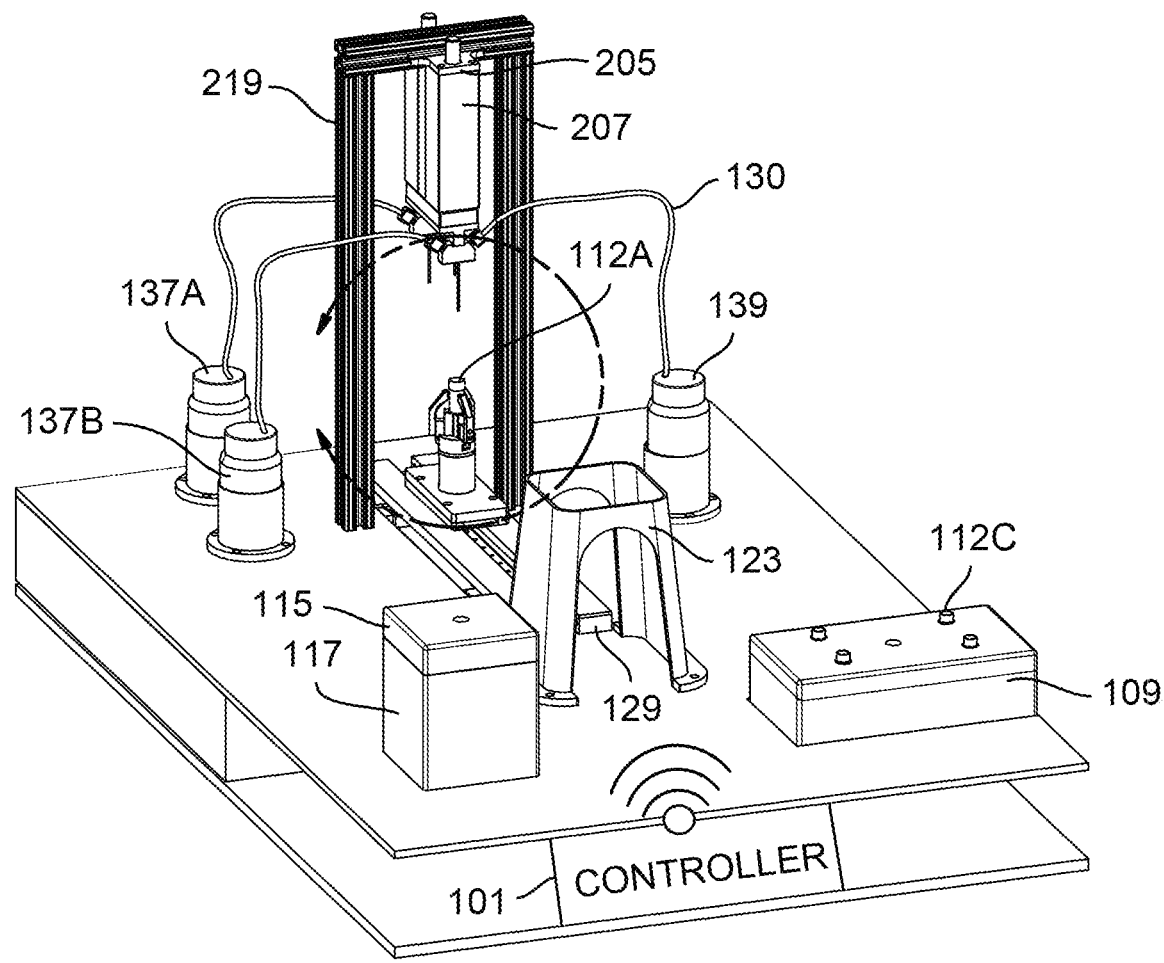
FIG. 4H is perspective diagram of the puncture station of the present teachings with needles preparing for puncturing the vial.
Figure 4H:
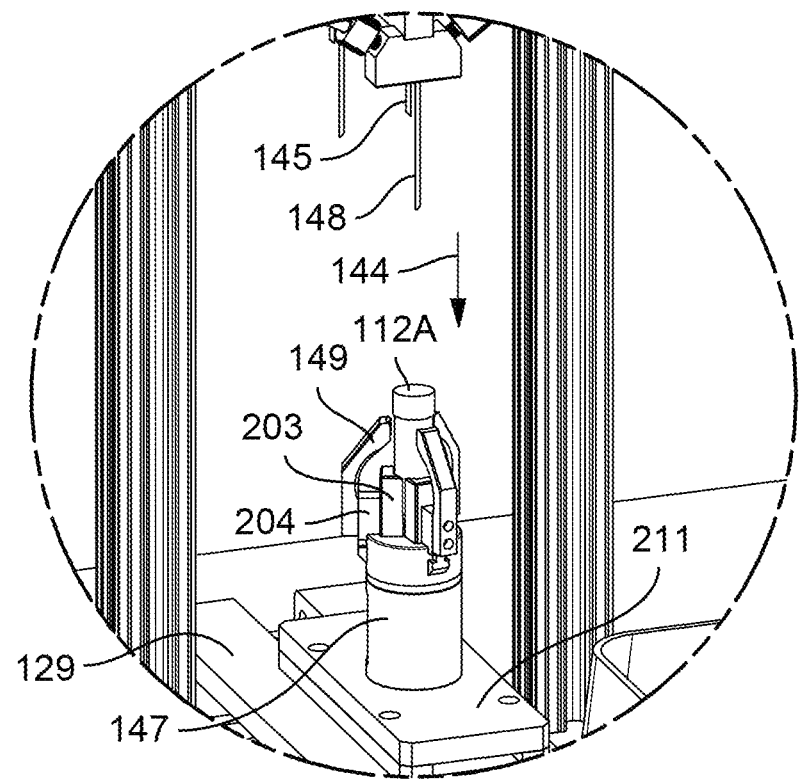
Figure 4I:
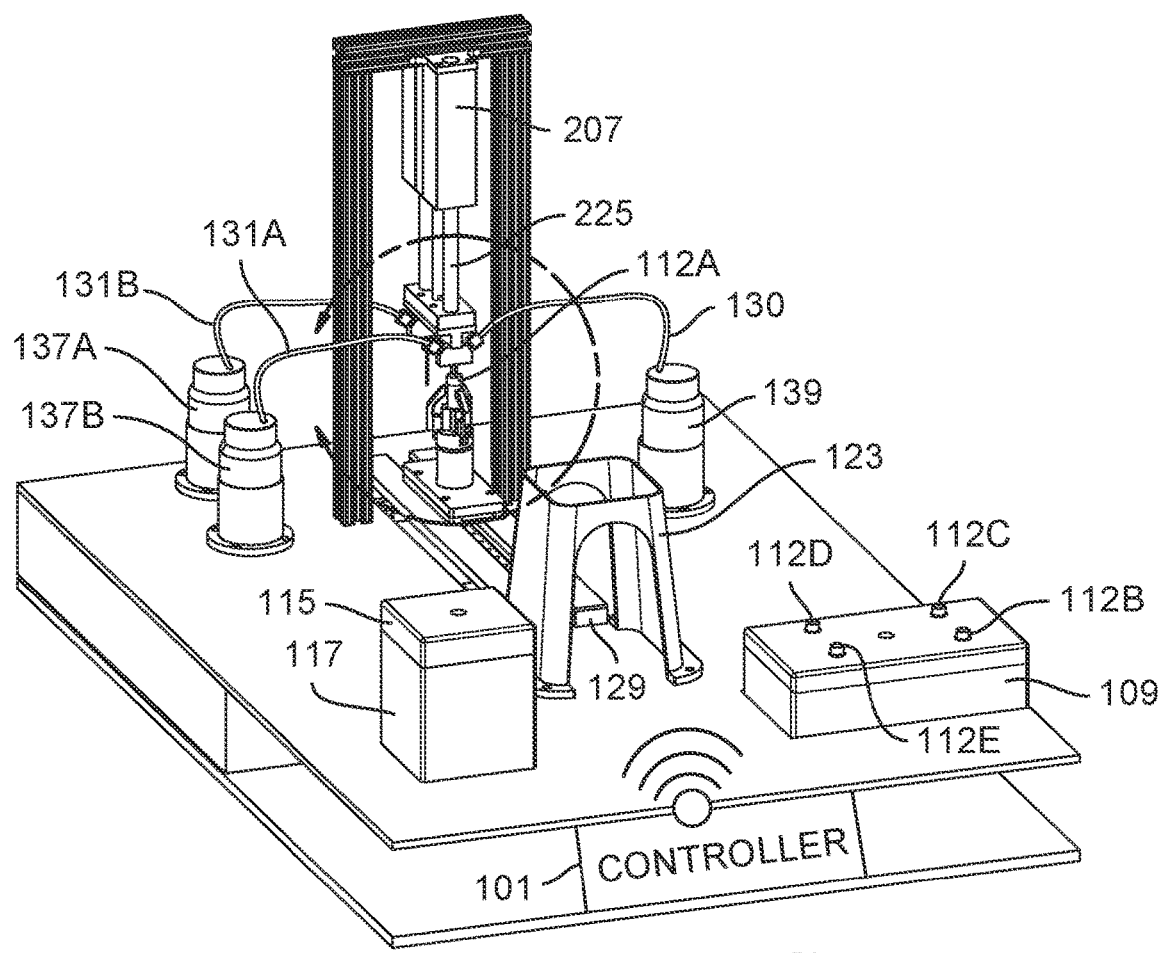
FIG. 4I is perspective diagram of the puncture station of FIG. 4H with needles puncturing the vial.
Figure 4I:
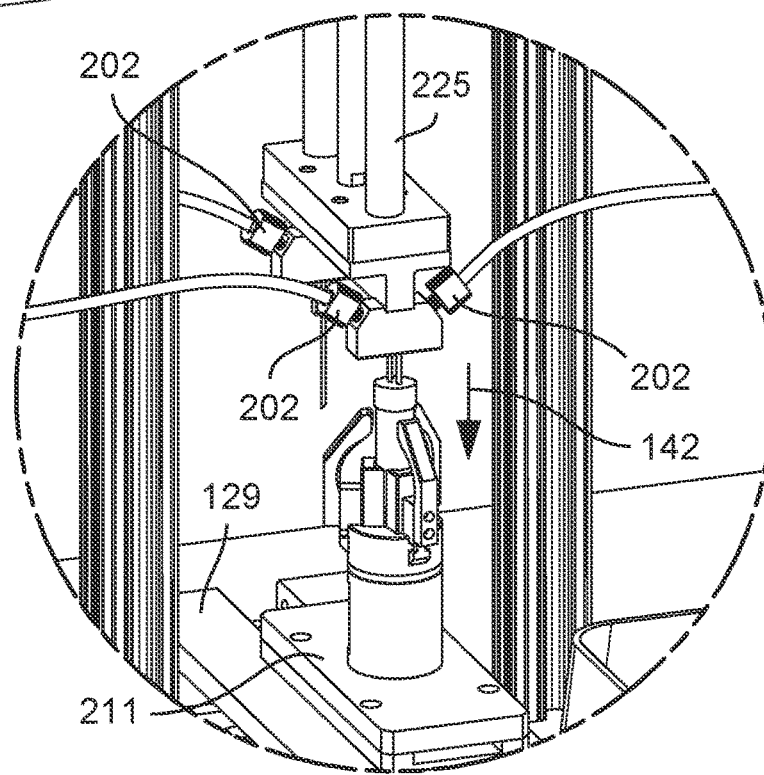

Referring now to FIGS. 4H and 4I, when decontamination has been completed, thaw controller 101 can instruct movement means 129 to move vial gripper system 147 and vial 112A, for example, through flaps 127 (FIG. 4F) into puncture station 143 (FIG. 4J) within hood 124. Thaw controller 101 can instruct movement means 129 to position vial gripper system 147 and vial 112A, for example, to insure that vial 112A is aligned in a pre-selected way with needles 145/148 (FIG. 4K). Puncture station 143 (FIG. 4K) can flush vial 112A, for example, with solution from solution reservoir 139 through tube 130 and connector 202 (FIG. 4K), while collecting displaced cells from vial 112A, for example, in cell reservoir 137. In some configurations, multiple vials 112A-112E can be punctured substantially simultaneously. In some configurations, connector 202 (FIG. 4K) can include a threaded luer lock fitting, for example, but not limited to, a 10-32 thread to female luer lock fitting. In some configurations, if it is desired to process a greater number of cells, larger vials can be accommodated by system 100. Thaw controller 101 can extend guided actuator 207 vertically based at least on the position of vial 112A, for example. In some configurations, when thaw controller 101 instructs movement means 129 to position vial gripper system 147 and vial 112A, for example, at a pre-selected position with respect to needles 145/148 (FIG. 4K), thaw controller 101 can elevate 144 (FIG. 4H) guided actuator rods 225. When vial puncturing is desired, thaw controller 101 can lower 142 (FIG. 4I) guided actuator rods 225.

Figure 4J:
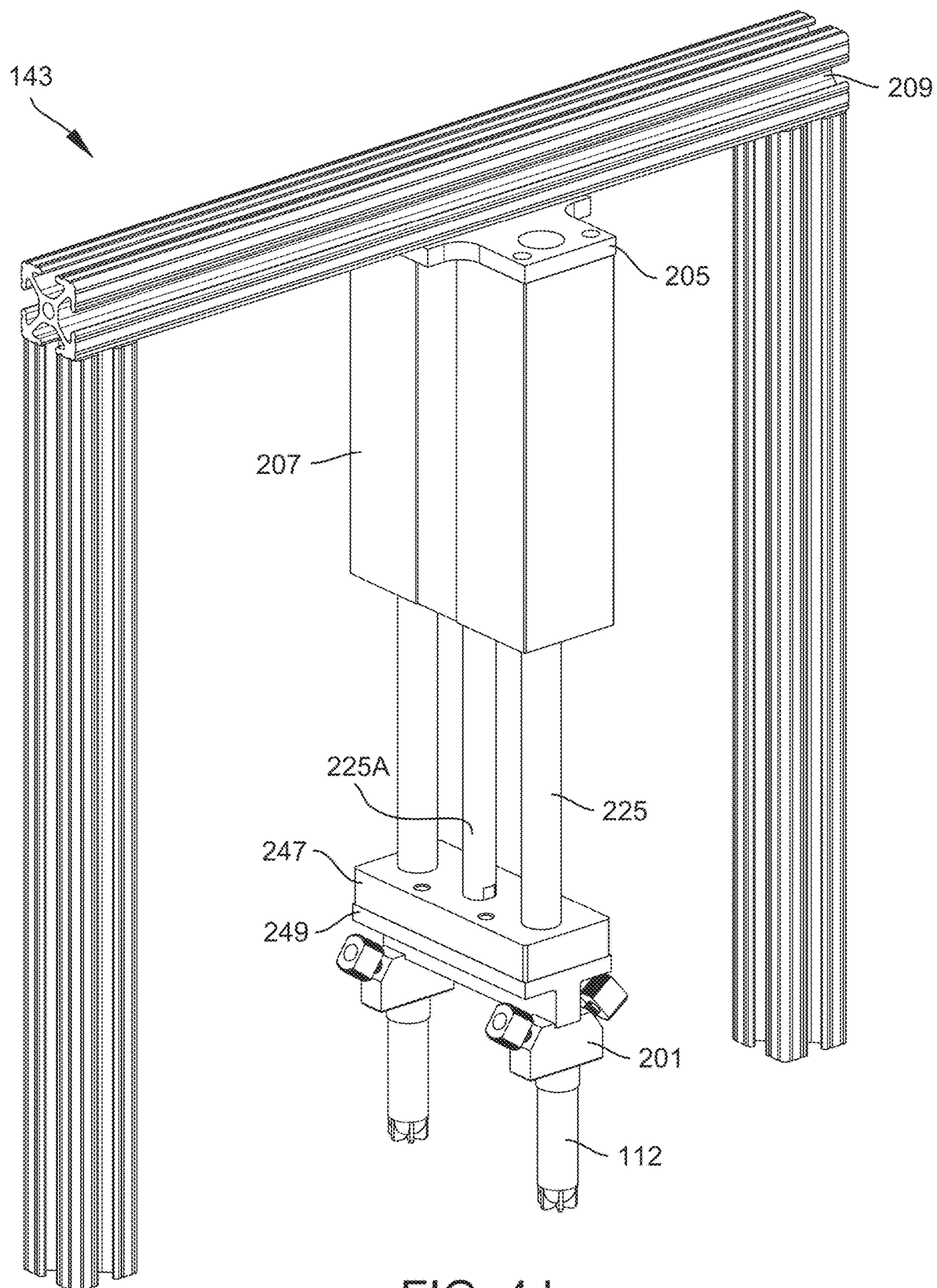
FIG. 4J is a perspective diagram of the puncture station of the present teachings.
Figure 4K:
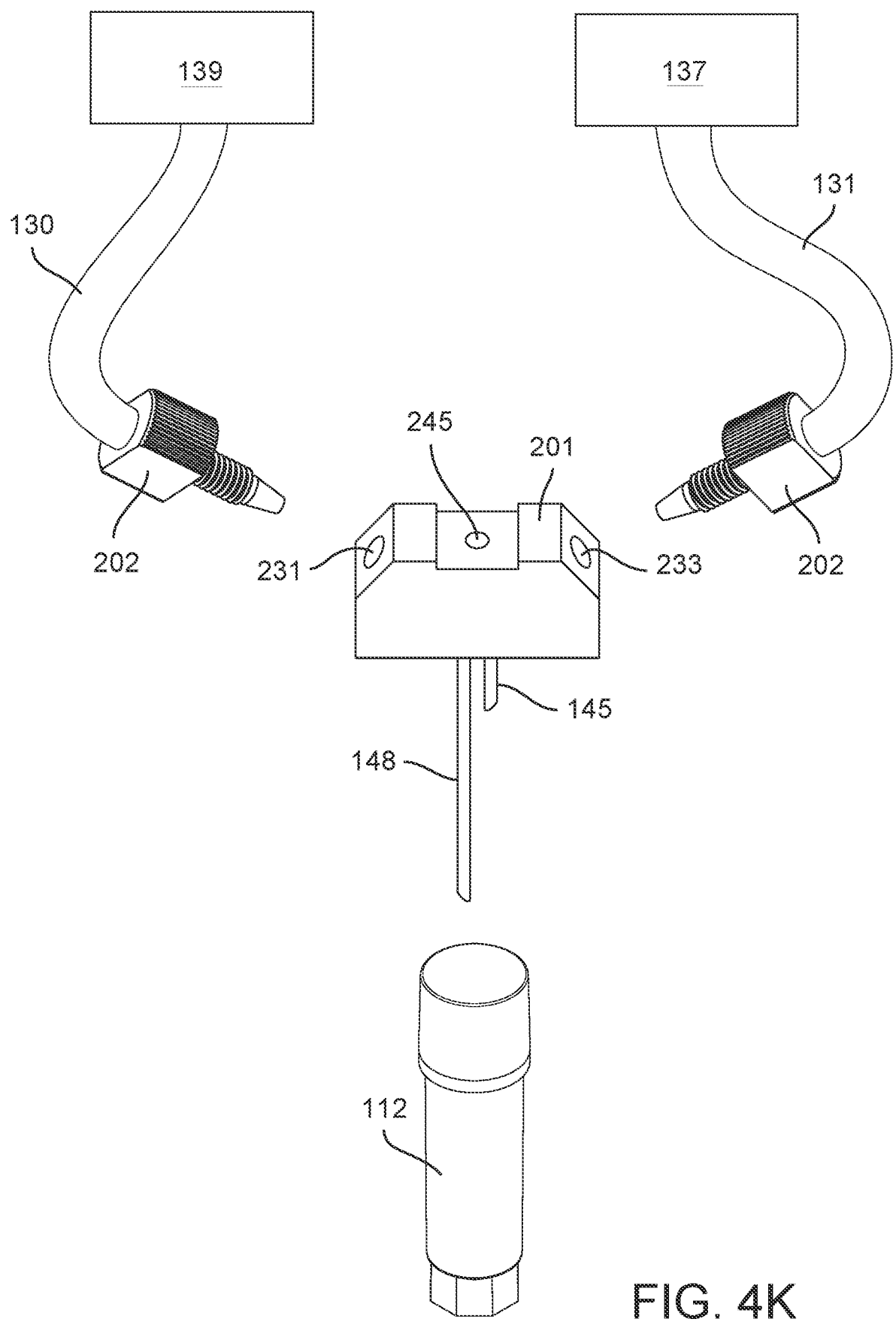
FIG. 4K is a perspective diagram of solution and cell reservoir connections.

Referring now to FIG. 4J, puncture station 143 can include, but is not limited to including, extrusion bracket 205, guided actuator 207, T bracket 249, vial puncture hub 201, and needles 145/148 (FIG. 4K). First ends of needles 145/148 (FIG. 4K) can be fitted into needle cavities (not shown) in T bracket 249. Second ends of needles 145/148 (FIG. 4K) can include beveled edges. Guided actuator 207, T bracket 249, and vial puncture hub 201 can be operably coupled by a fastener passing from pole connector 247 through T bracket 249 to cavity 245 (FIG. 4K) in vial puncture hub 201. Guided actuator poles 225 can travel into and out of guided actuator 207 under pressure by a puncture cylinder (not shown), which can be operably coupled with extrusion 209 through extrusion bracket 205. Extrusion 209 and extrusion bracket 205 can enable flexible horizontal positioning of guided actuator 207 and therefore needles 145/148. Guided actuator 207 can include, but is not limited to including, a commercially-available actuator such as, for example, but not limited to, FESTO® Guided Actuator DFM-25-80-P-A-KF, or any actuator that includes high resistance to torques and lateral forces. In some configurations, guided piston rod 225A can be secured against rotation by guide rods 225. Guide rods 225 can also assist in enabling multiple simultaneous and/or semi-simultaneous punctures of multiple vials 112. In some configurations, to properly puncture vial 112, the puncture cylinder (not shown) can provide puncture force in the range of 5-7 kgf. Guided piston rod 225A can include a cylinder bore of between about 10 mm and 20 mm, and, at a supply pressure in the range of between about 4 and 7 bar, can supply a force of between about 70N to 220N. In some configurations, a minimum force of greater than 60N can be produced.

Figure 4L:
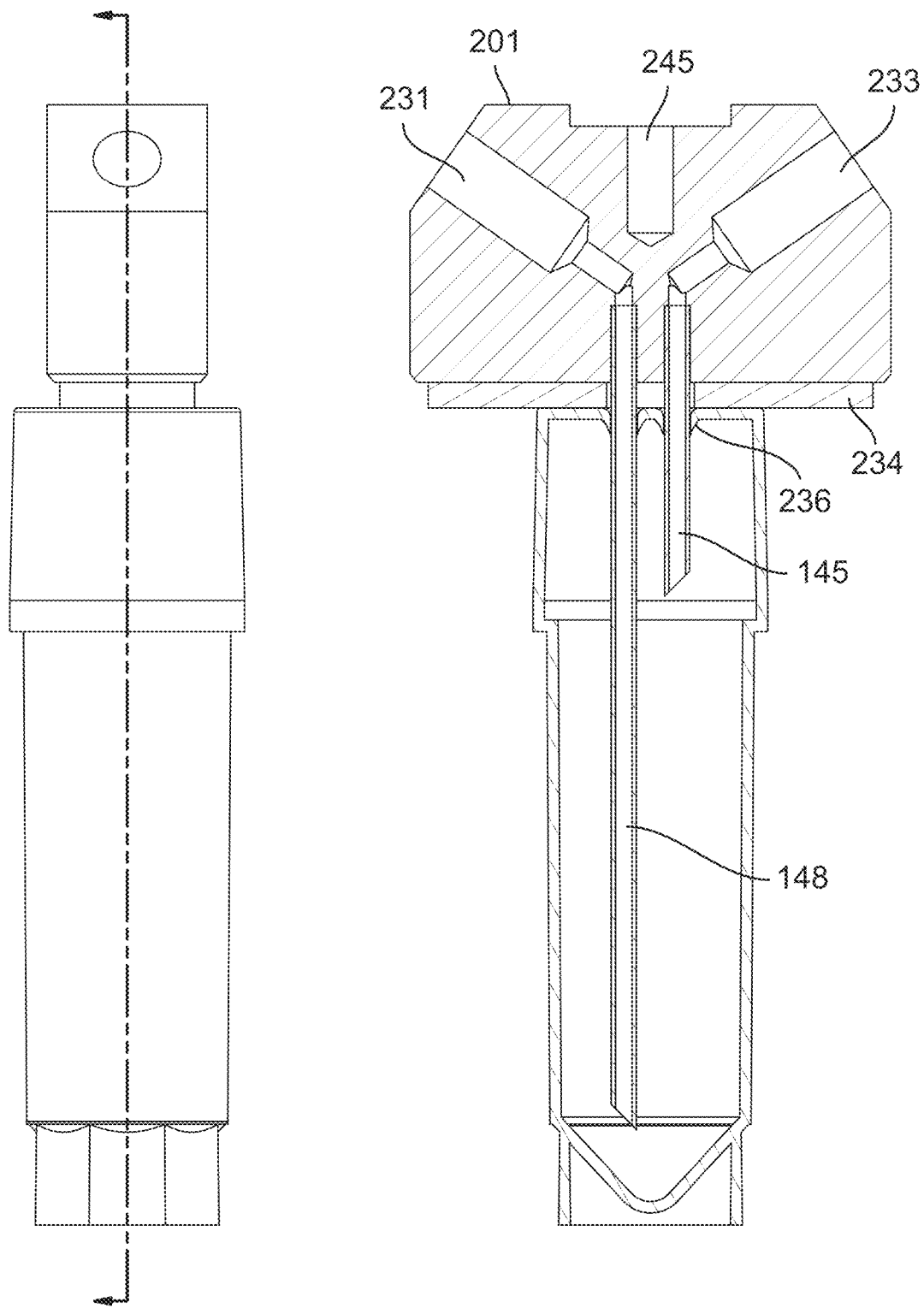
FIG. 4L is a cross section diagram of the vial puncture hub of the present teachings.

Referring now to FIGS. 4K and 4L, vial puncture hub 201 can include vial puncture fitting cavities 231/233 that can accept vial puncture fittings 202. A first vial puncture fitting 202 and solution tube 130 can provide an interface between solution reservoir 139 and needle 148. A second vial puncture fitting 202 and cell tube 131 can provide an interface between cell reservoir 137 and needle 145. In some configurations, thaw controller 101 can instruct a pump (not shown) to move solution from solution reservoir 139 through solution tube 130 and the first vial puncture fitting 202, vial puncture hub 201, and into needle 148. Solution within vial 112 can force the thawed cells present in vial 112 into needle 145, through vial puncture hub 201, the second vial puncture fitting 202, cell tube 131, and ultimately into cell reservoir 137. In some configurations, needles 145/148 can include 316 stainless steel, and the beveled edges of needles 145/148 can be clocked in opposing directions, ±10°. In some configurations, vial puncture holes 231/233 can include dimensions, for example, but not limited to, about 0.0605+0.0015, -0.0008 inches, and tubes 129/131 can include bore size in the range of about 0.03 to 0.06 inches. With respect to needles 145/148, the inner diameter can be chosen to be large enough to achieve reasonable flow rates, and to avoid excessive shear on the cells and/or long pumping times. Appropriate needle wall thickness can ensure that needles 145/148 can puncture the cap of vial 112 without buckling, for example, in the range of between about 0.008 to 0.015 inches. In some configurations, both needles 145/148 can include a soldered or brazed joint diametric clearance with respect to vial puncture hub 201 of about 0.0035 inches. In some configurations, vial puncture hub 201 can include 316 stainless steel.

Referring now to FIG. 4L, vial puncture hub 201 can include gasket 234 that can, in conjunction with deformation 236, prevent cell leakage, i.e. prevent cells that are evacuating vial 112 from taking a route other than through one of needles 145/148. Puncturing vial 112 can puncture gasket 234 forming deformation 236 along with a leak-proof seal.

Figure 5:
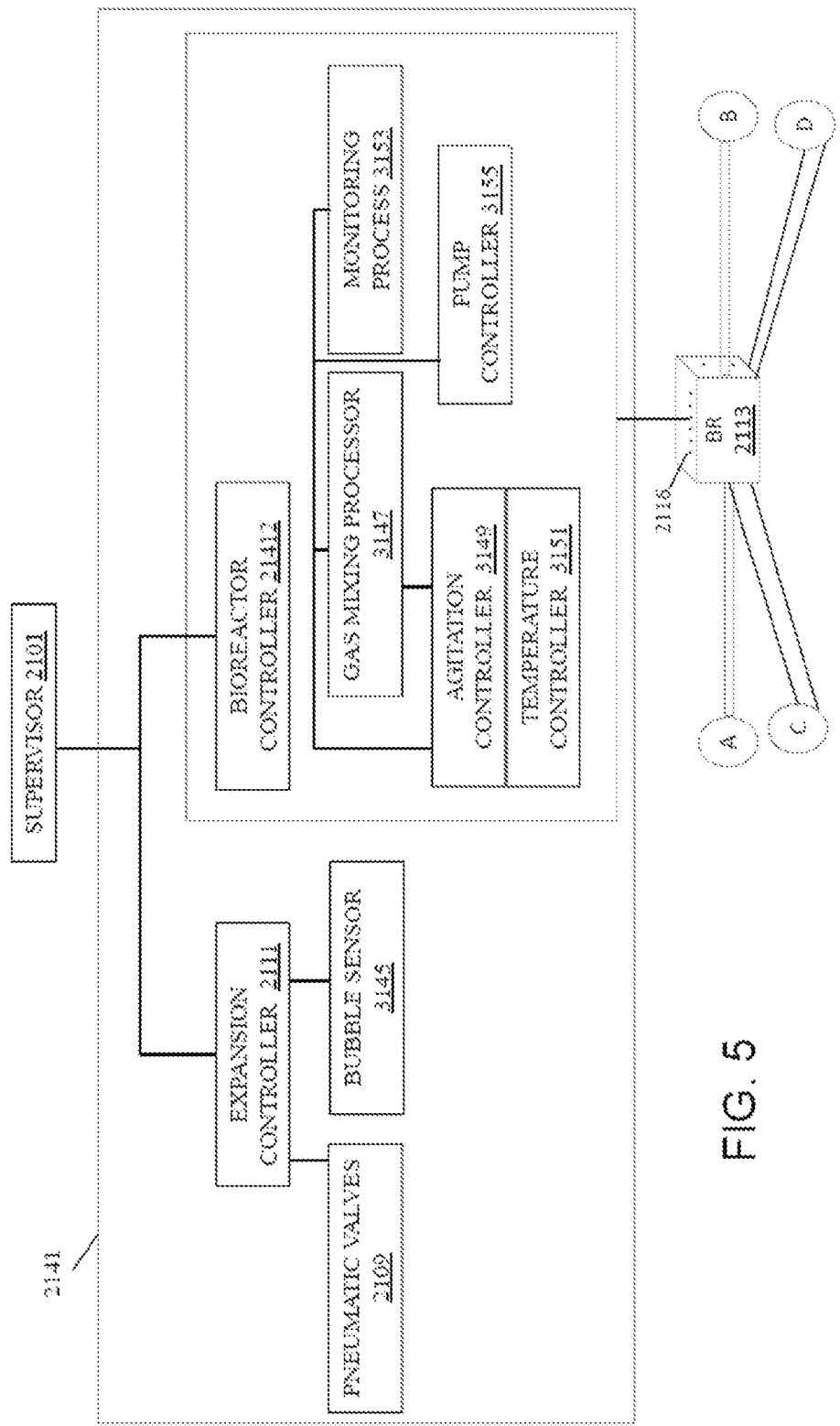
FIG. 5 is a schematic block diagram of the expansion subsystem under control of the supervisor of the present teachings.

Referring now to FIG. 5, after the cells are thawed, if cell thawing is necessary, supervisor 2101 can enable movement of cells and transfer of control from thaw subsystem 2147 (FIG. 4) to expansion subsystem 2141. Expansion subsystem 2141 can include expansion controller 21411 and bioreactor controller 21412. Expansion controller 21411 can control fluid and pneumatic valves 2109 that can enable control of the direction fluid is pumped from one place to another. Expansion controller 21411 can monitor, through bubble sensor 3145, priming and the leading edge of the fluid in the tubing between vial 2163 (FIG. 4) and bioreactor vessel(s) 2113. Cell transfer from vial 4163 (FIG. 4) to bioreactor vessel(s) 2113 can be deemed complete when a pre-selected amount of time, or range of times, has expired. In some configurations, part of the transfer can be done by pumping, and part can be done with a gas purge. Cells can be moved from vial 4163 (FIG. 4) to bioreactor vessel(s) 2113, where they can attach to, for example, but not limited to, microcarrier(s) 2116 within bioreactor(s) 2113. Cell growth enablers other than microcarriers 2116, or none at all, are possible. For example, some cells grow as cluster aggregates. Bioreactor controller 21412 can enable the sequencing of gas mixing 3147, agitation 3149, and temperature control 3151 of the contents of bioreactor(s) 2113. Stepper motors can be used to agitate bioreactor(s) 2113. Bioreactor controller 21412 can control the movement of media and cells through pump controller 3155 that can enable pumping media from reservoir 6149 to bioreactor(s) 2113 and from bioreactor(s) 2113 to waste. Bioreactor(s) 2113 can be agitated by agitation controller 3149, and temperature controller 3151 can enable adjustment of the temperature of the media. Gas mixing processor can enable control of gas in the media, and therefore control the characteristics of the media. Monitoring process 3153 can monitor the characteristics of the media in bioreactor(s) 2113. Characteristics of the media that can be monitored can include, but are not limited to including, temperature, dissolved oxygen, and pH. The cell density in bioreactor(s) 2113 can be monitored, as a pre-selected target range for cell density can trigger the end of cell expansion in a particular bioreactor.

Continuing to refer to FIG. 5, expansion controller 21411 can include, for example, but not limited to, a ROCKWELL AUTOMATION® COMPACTLOGIX® controller that can control pneumatic valves 2109 and bubble sensors 3145 through a FESTO® valve terminal. Bioreactor controller(s) 21412 can include, but is not limited to including, EPPENDORF® DASGIP® controller(s), or any type of bioreactor controller that can operate multiple bioreactors in parallel. Bioreactor controller(s) 21412 can control and monitor bioreactor temperature and agitation. Temperature control can be enabled by, for example, but not limited to, EPPENDORF® DASGIP® Bioblock control. Media pH, dissolved oxygen, liquid level, and cell density can be monitored by a monitoring module reporting data to bioreactor controller(s) 21412. The state of gas mixing valves, that can control the change in carbon dioxide and ultimately the change in pH, can be controlled by gas mixing processor 3137 answering to bioreactor controller(s) 21412. In some configurations, % $CO_2$, % $O_2$, and gas flow rate out of the headspace of bioreactor vessel 2114 can be measured, and oxygen consumption rate can be determined. Media addition/removal can be monitored and controlled by peristaltic pump(s) at a pump rate that can be adjusted by bioreactor controller(s) 21412 based on data monitored by bioreactor controller(s) 21412.

Figure 6:
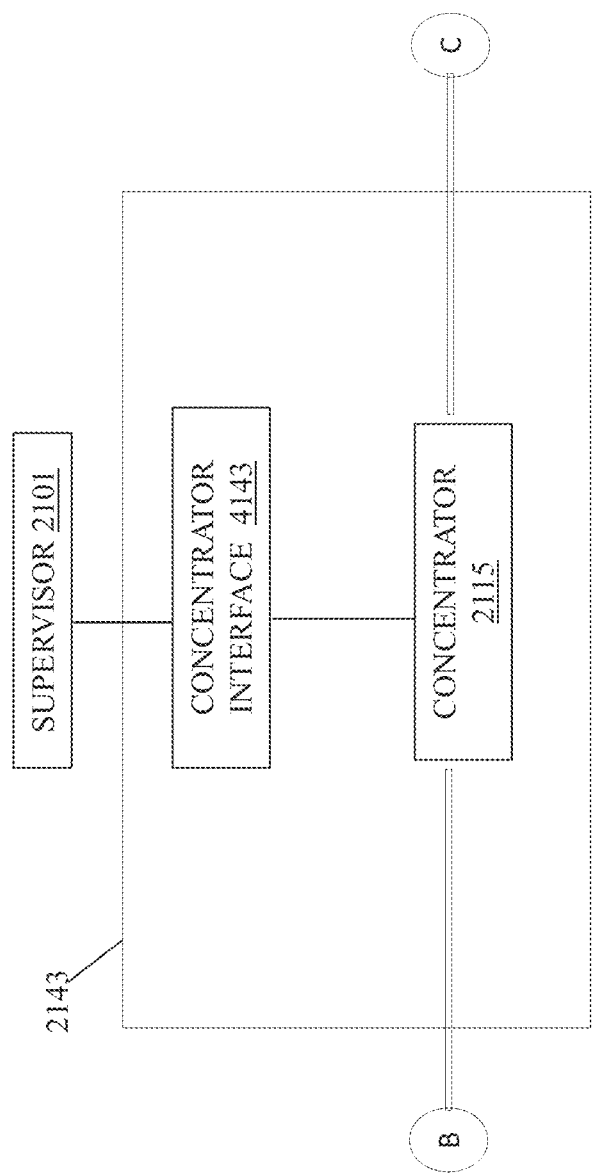
FIG. 6 is a schematic block diagram of the concentration subsystem under control of the supervisor of the present teachings.
Figure 7:
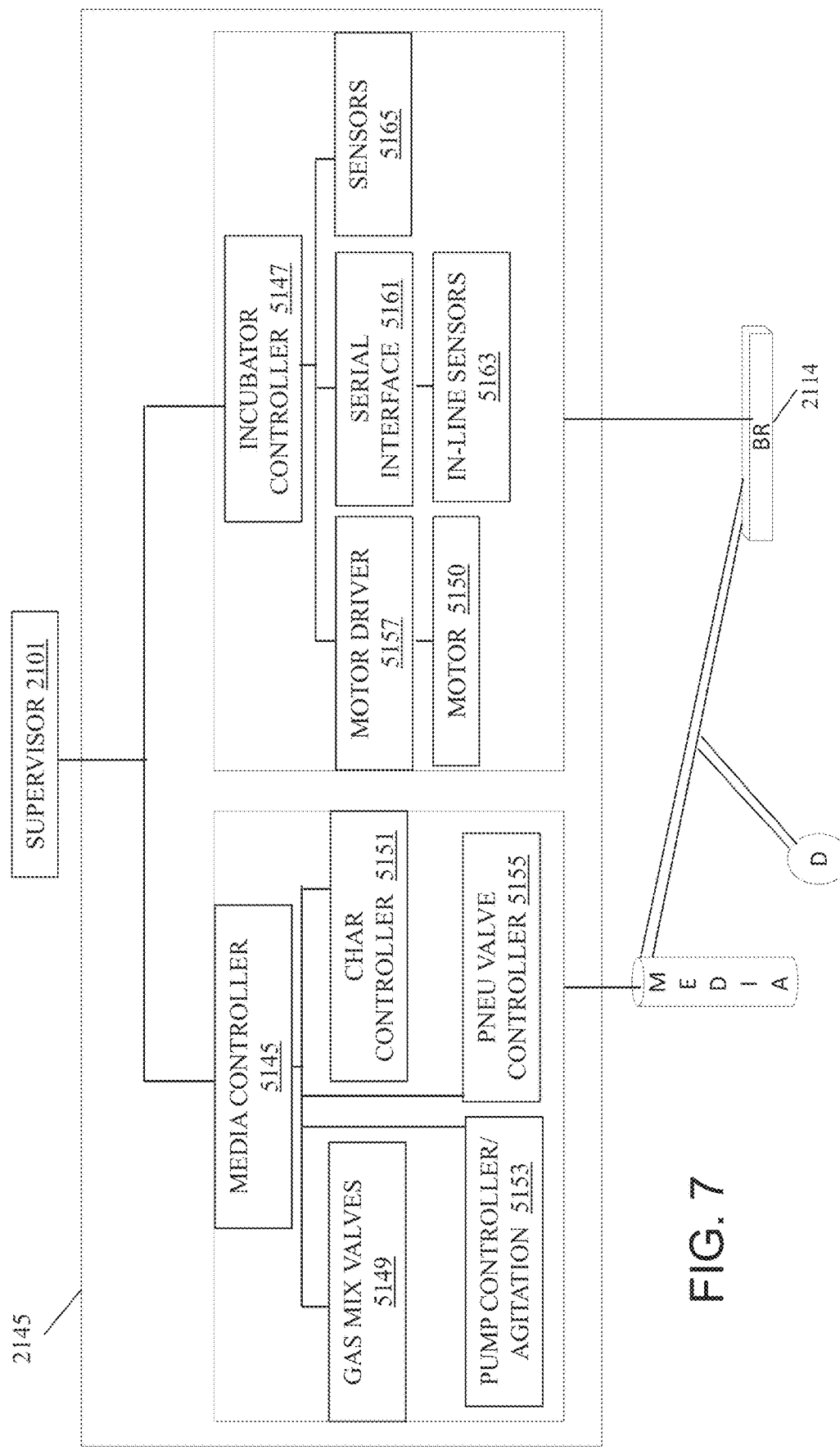
FIG. 7 is a schematic block diagram of the maturation subsystem under control of the supervisor of the present teachings.

Referring now to FIG. 6, when cell density reaches a desired level, possibly set out in a recipe, the resulting expanded cells can be subjected to concentration in another station along the production line, concentration station 2143. Supervisor 2101 can detect, from data monitored by expansion subsystem 2141 (FIG. 5), cell density, and can enable moving cells into concentration subsystem 2143 where the expanded cells can be concentrated, possibly by centrifugation. In some configurations, expanded cells can be pumped into concentration subsystem 2143, concentrated, and moved back to expansion subsystem 2141 (FIG. 7). In some configurations, concentration subsystem 2143 can provide, but is not limited to providing, cell concentration and media clarification through live cell separation from dead cell and detritus. In some configurations, concentration subsystem 2143 can include, but is not limited to including, CARR® CENTRITECH® LAB III. In some configurations, supervisor 2101 can interface with concentration subsystem 2143 through concentrator interface 4143. In some configurations, concentrator interface 4143 can provide a protocol that is specific to industrial systems that communicate over industrial Ethernet to control equipment, such as concentrator 4145, in industrial systems. In some configurations, the protocol can include Profinet, an industry technical standard for data communication.

Referring now to FIG. 7, when a concentration cycle is complete, supervisor 2101 can enable cells to be moved from concentrator subsystem 2143 to expansion subsystem 2141 for concentration adjustment, then on to maturation subsystem 2145. The length of the concentration cycle can be pre-selected, set by a user, dependent upon cell type, set in a recipe, and/or dynamically determined based on data collected during the concentration cycle. Maturation subsystem 2145 can include, but is not limited to including, media controller 5145 and incubator controller 5147. In some configurations, supervisor 2101 can enable cells to be moved from concentrator subsystem 2143 to expansion subsystem 2141 for concentration adjustment, and then transfer to maturation subsystem under control of incubator controller 5147. Media can be moved to vessel(s) 2118, under the control of media controller 5145. Media controller 5145 can adjust the characteristics of the media in vessel(s) 2118, agitate the media, and pump the media to bioreactor(s) 2114.

Characteristics controller 5151 can adjust the characteristics of the media, such as, for example, but not limited to, temperature, pH, and dissolved oxygen. Gas mix valves 5149 can provide gas that can be required to adjust, for example, the pH. Pump controller 5153 and pneumatic valve controller 5155 can enable movement of media from reservoir 6149 (FIG. 8) to vessel(s) 2118, and from vessel(s) 2118 to bioreactor 2114. Within bioreactor 2114 are surfaces to which cells can attach while they are maturing. A first type of cell can be introduced from vessel(s) 2118, and they can adhere to one side of the surface(s). Incubator controller 5147 can command motor driver 5157 to enable motor 5159 to rotate the surface(s) and a second cell type can be introduced. In this way, two types of cells can be maturing simultaneously, and the geometry of bioreactor 2114 can encourage the cells to grow together. Incubator controller 5147 can receive data from in-line sensors 5163 through serial interface 5161, for example, and can also receive data from sensors 5165. Many things can be sensed with respect to the maturing cells, such as, for example, temperature, pH, and glucose. Supervisor 2101 can raise alerts if the sensed data fall outside of acceptable ranges. In some configurations, supervisor 2101 can enable adjusting the environment of bioreactor(s) 2114 based upon the sensed data.

Continuing to refer to FIG. 7, after the concentrated cells are prepared for maturation, incubator controller 5147 can exchange messages with motor drivers that control the movement of bioreactor(s) 2114. Incubator controller 5147 can include, but is not limited to including, a ROCKWELL AUTOMATION® COMPACTLOGIX® controller. Motor driver 5157 can include stepper motor 5159 for industrial systems, for example, but not limited to, an ANG1 AnyNET-I/O integrated stepper motor controller/driver. At maturation subsystem 2145, incubator controller 5147 can monitor the characteristics of the cells and fluid surrounding them as they mature. In some configurations, in-line sensors 5163 can be used to monitor pH, dissolved oxygen, and glucose, possibly through a serial interface. Other sensors can monitor relative humidity, temperature, carbon dioxide concentration, and incubator alarms.

Figure 7A:
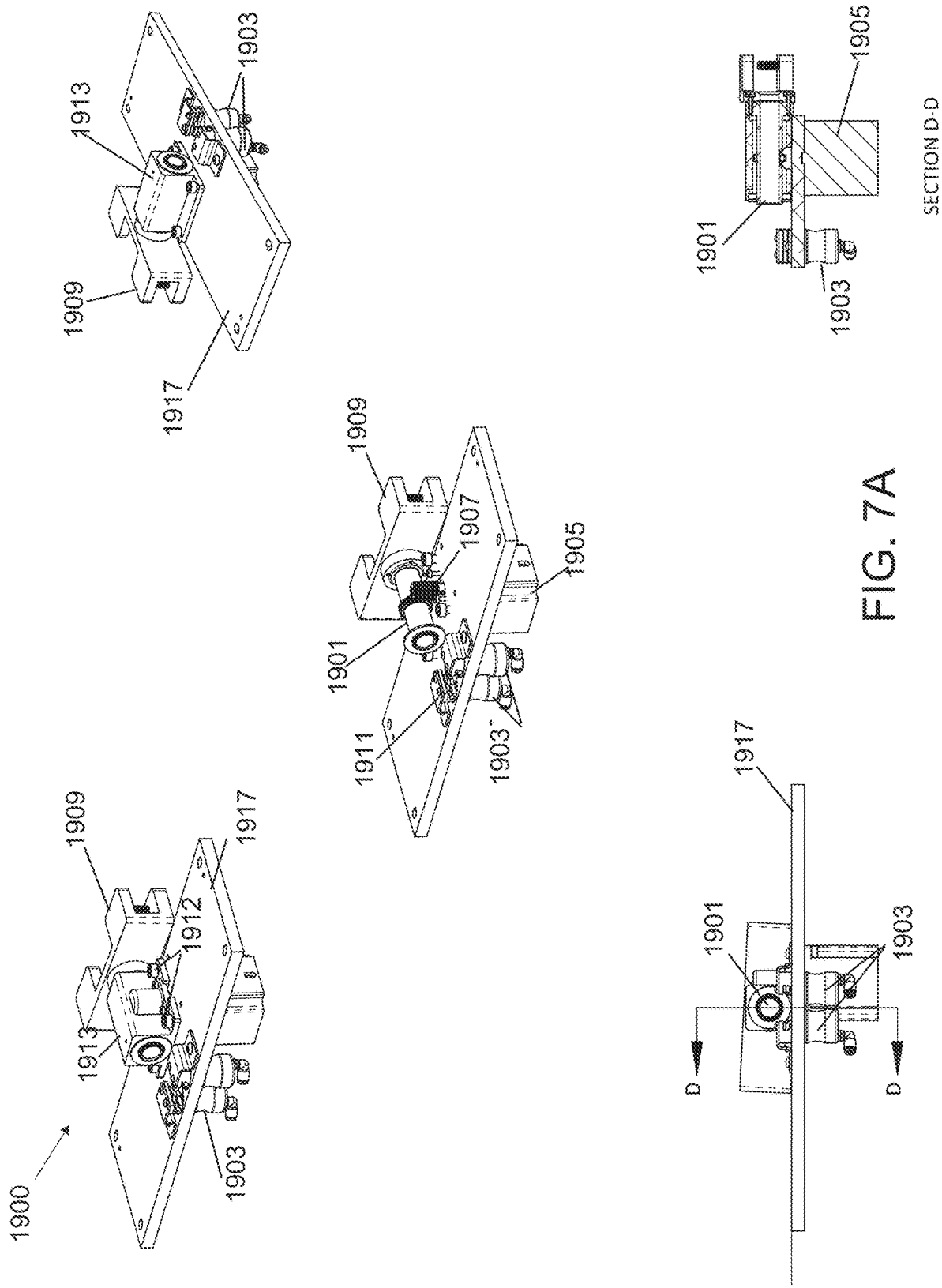
FIG. 7A is a perspective schematic view of the rotational device of the present teachings.
Figure 7B:
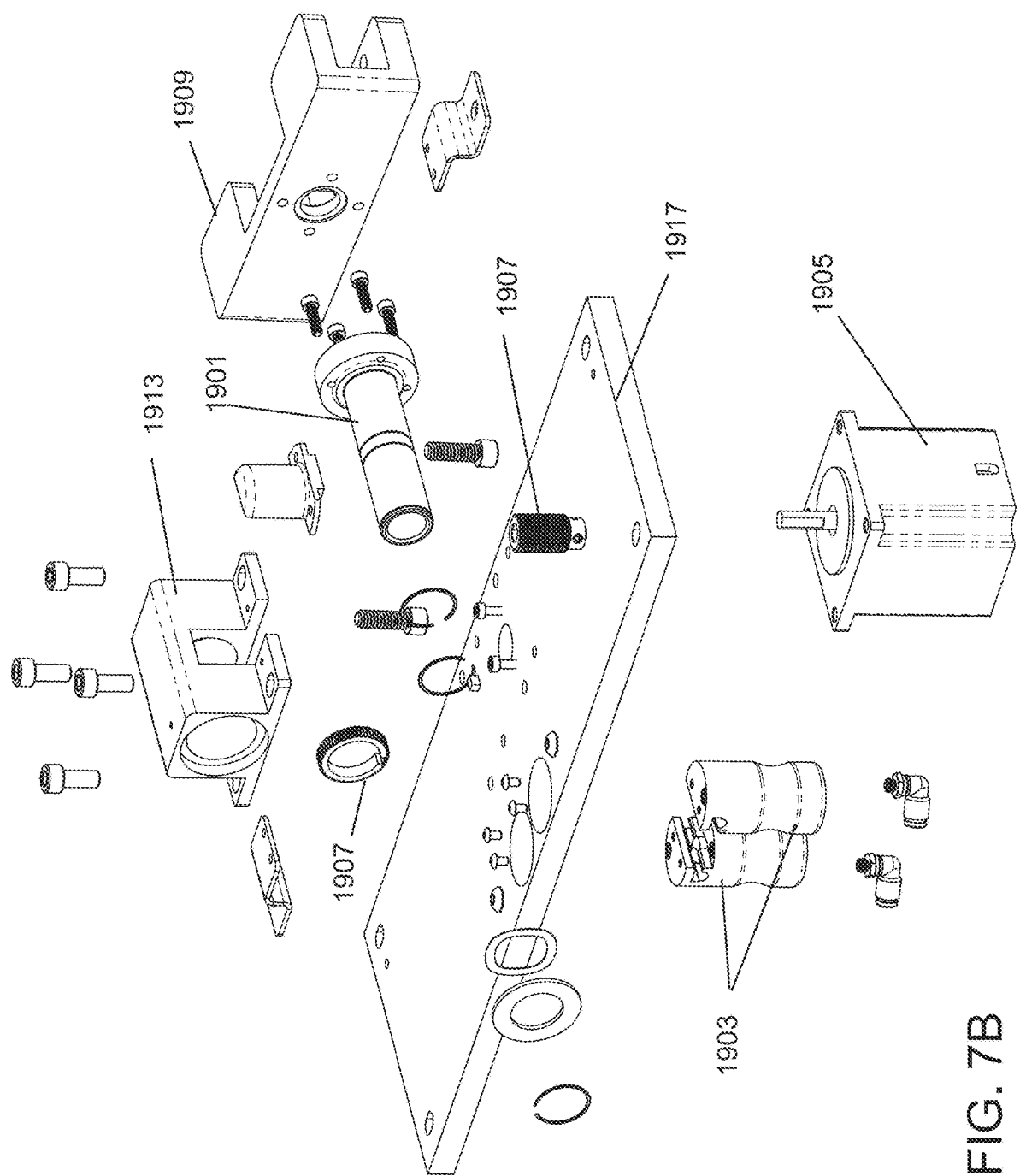
FIG. 7B is an exploded schematic view of the rotational device of FIG. 7A.

Referring now to FIGS. 7A and 7B, the rotation of bioreactor 2114 can be managed by rotational device 1900. Rotational device 1900 can accommodate any shape and size of bioreactor 2114, possibly by modifying the dimensions of rotational device 1900, if necessary. Rotational device yoke 1909 can provide cantilevered support to bioreactor 2114, allowing unobstructed observation of samples. Rotational device 1900 can enable cell and media supply and gas venting tubing to remain intact and untangled throughout a limited operational rotation range of bioreactor 2114, for example +/−270 degrees. Rotational device 1900 can include, but is not limited to including, hollow spindle 1901 that can accept and protect tubing 1919A/B/C as bioreactor 2114 rotates. Hollow spindle 1901 can be held in place by spindle cover 1913, mounted atop mounting board 1917. Worm wheel and worm screw 1907 can enable rotation of yoke 1909/bioreactor 2114 combination while tubing 1919A/B/C remains within hollow spindle 1901 and untangled, and reducing inertial concerns during rotation. Motor 1905 can enable worm screw and worm wheel 1907 to rotate yoke 1909. Bolts 1912 can accommodate a gear cover for worm screw 1907 that can shroud worm screw 1907 and protect the device and process from metal-on-metal particulate emission. The rest of rotation device 1900 can be wash-down rated, for example, to the IEC 60529 IP65 standard.

Referring now to FIG. 7C, bioreactor 2114 can be seeded through either of tubes 1919B or 1919C depending upon the orientation of bioreactor 2114. In the view shown in FIG. 7C, bioreactor side 2114A can receive cells and media through tube 1919B, while pinch valve 1903 that is associated with tube 1919B can be forced to open. Pinch valve 1903 that is associated with tube 1919A can close on tube 1919A. Cells and media can enter bioreactor interior 1920 through tube 1919B, and can be encouraged by gravity to adhere to side 2114A of bioreactor 2114. Tube 1919A can enter bioreactor 2114 through cavity 2114C, centrally located on bioreactor side 2114B, for example. Tube 1919B can enter bioreactor 2114 through cavity 2114D, laterally located on bioreactor side 2114A, for example. Entry locations 2114C/D can be located to encourage one type of cell to grow around another type of cell. For example, a first cell type can be seeded through cavity 2114D, and a second cell type can be seeded through cavity 2114C, thus encouraging the first cell type to grow around the second cell type.

Figure 7D:
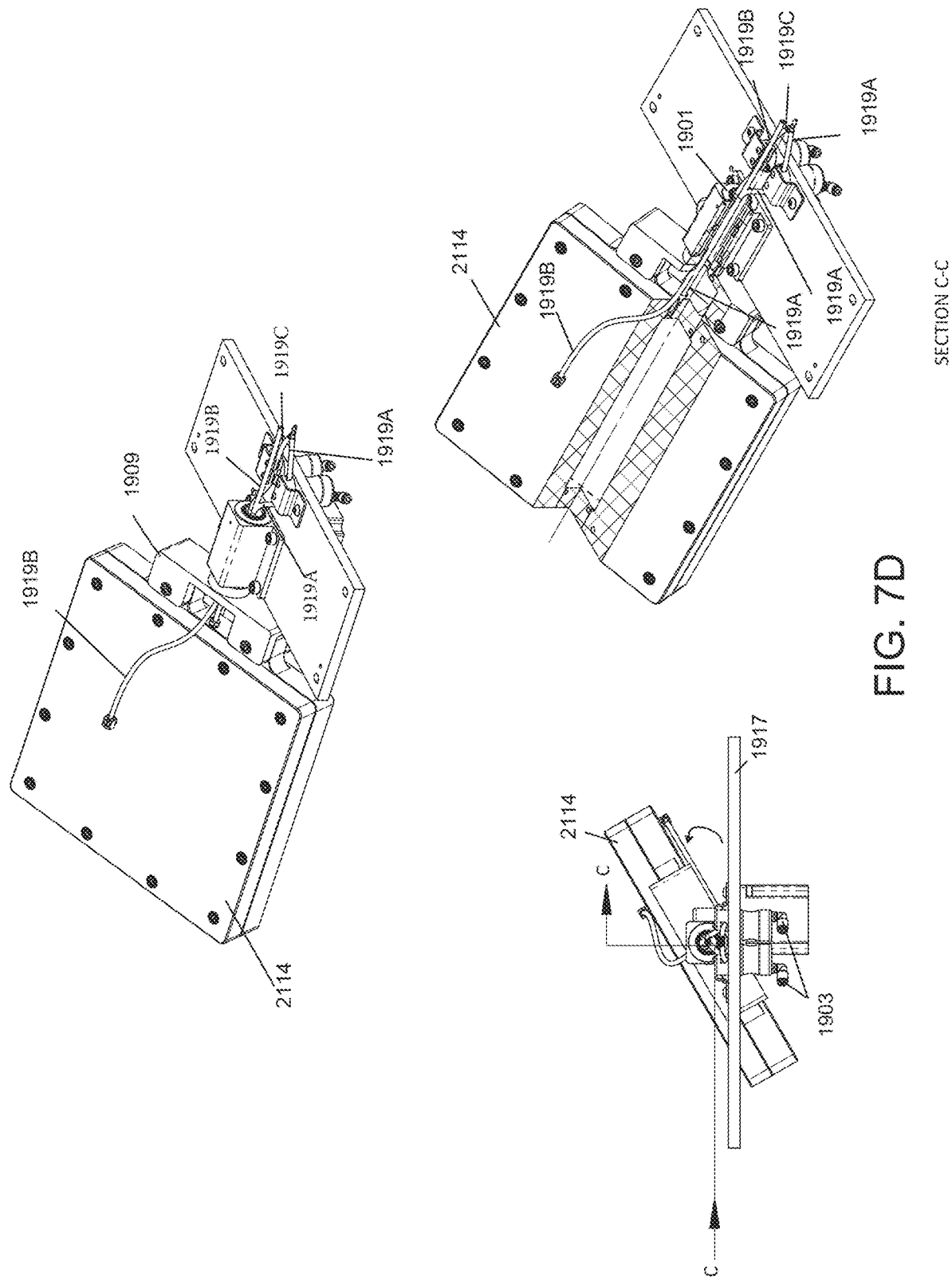
FIG. 7D is a cross-sectional view of the rotational device of FIG. 7A coupled with a bioreactor in a second position.

Referring now to FIGS. 7C-7E, operationally, after bioreactor 2114 is seeded, worm screw 1907 can accommodate a slight tilt in yoke 1909 (and bioreactor 2114), for example, up to about 3°, followed by a temporal dwell, to provide even liquid distribution and encourage consistent cell seeding density and attachment to bioreactor side 2114B. Worm gear 1907 can return yoke 1909 to a horizontal position to allow attachment to take place, and can retilt if desired. Eventually, worm screw 1907 can rotate so that yoke 1909/bioreactor 2114 rest at 180° from their starting position. At this time, cells can be seeded onto side 2114A of bioreactor 2114 through tube 1919A. The amount of time required for each step is dependent on the type of tissue desired, the process to form that tissue, and other considerations. Any gas produced during seeding and maturation can be vented through tube 1919C, which can be terminated in a filtered exhaust opening.

Continuing to refer to FIGS. 7C-7E, to harvest the tissue, bioreactors 2114 can be arranged in a rack, and the entire rack can be removed from the incubator. The incubator can include, but is not limited to including, a welded stainless steel assembly that can be sanitized between uses. The incubator can house the controller for the motors and can include a network connection. Rotation devices 1900 can be configured to operate in pairs in which bioreactor 2114 could be cantilever supported at one driven side, and simply supported at a second side.

Referring now to FIG. 8, supervisor 2101 can control aspects of media reservoir 6149, for example. In some configurations, media reservoir 6149 can be located in environment-controlled area 6145, reducing the possibility of degradation of thermally-sensitive supplements in the media.

Figure 9B:
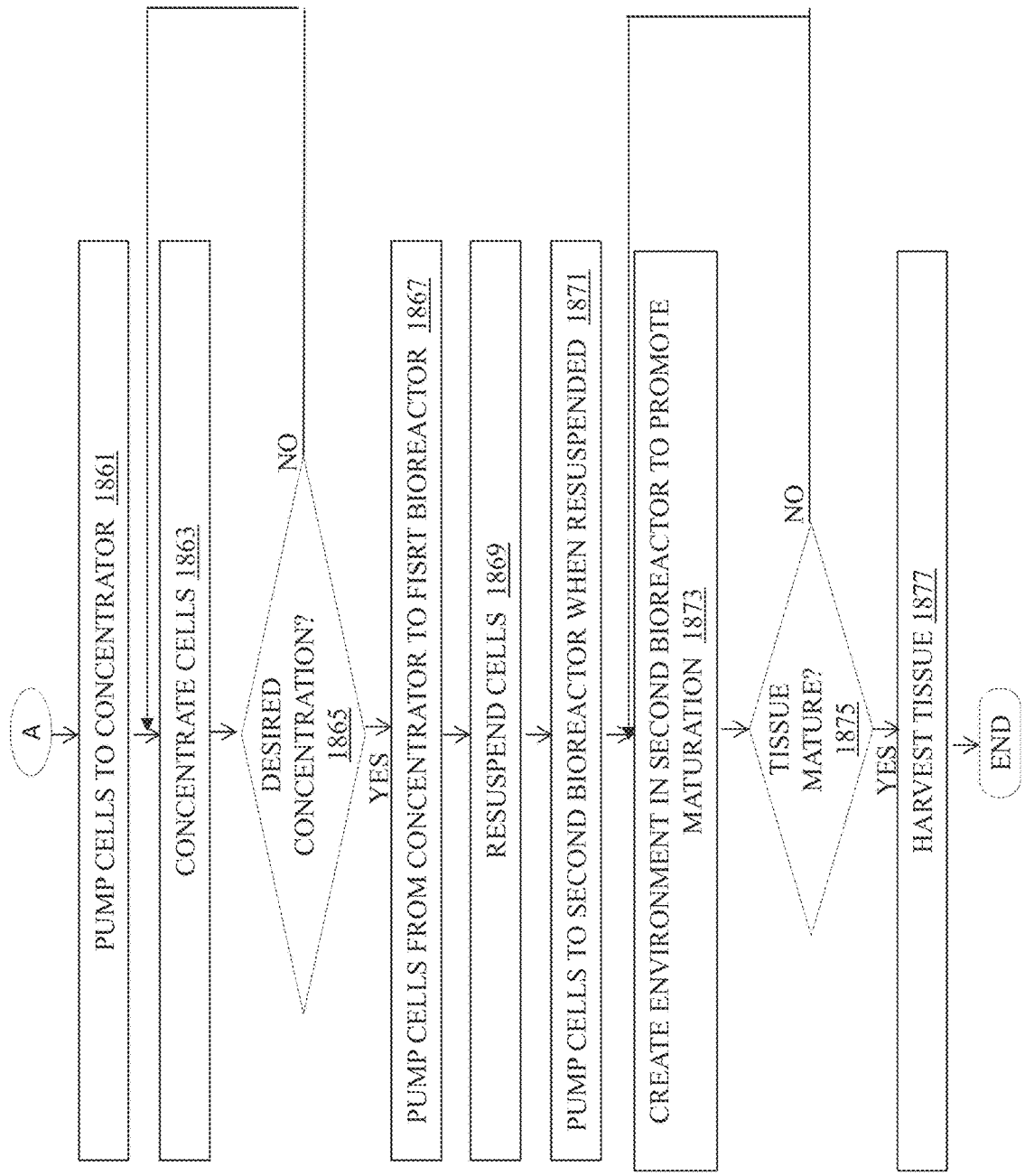

Referring now to FIGS. 9A and 9B, method 1850 of the present teachings for manufacturing tissue along a production line can include, but is not limited to including, pumping 1851 cells from the at least one vial to at least one first bioreactor. When 1853 the cells are moved to the at least one first bioreactor, method 1850 can include managing 1855 fluid flow between the at least one vial and the at least one bioreactor, and creating 1857 an environment enabling draining, washing, digesting, and quenching processes to promote cell expansion in the at least one first bioreactor. The environment can be automatically created and automatically maintained based on sensor data of critical process parameters. When 1859 a desired cell density in the at least one first bioreactor is reached, and when other processes are complete, method 1850 can include pumping 1861 the expanded cells to a concentrator and concentrating 1863 the cells. When 1865 the cells are at a desired concentration, method 1850 can include pumping 1867 the concentrated cells to at least one first bioreactor, resuspending 1869 the concentrated cells, and pumping 1871 the resuspended cells to at least one second bioreactor for seeding and maturation. Method 1850 can include creating 1873 an environment in the at least one second bioreactor to promote maturation based upon monitoring of sensor data of critical process parameters, among other parameters. After tidal exchanges, media refresh, washes, digestion, and media swaps for differentiation, and when 1875 the cells have reached a desired maturity, method 1850 can include harvesting 1877 tissue resulting from the matured cells.

In some configurations, the sequence of steps taken under automatic control by supervisor 2101 (FIG. 1) (except where human input is desired in the preparation stage—steps 7, 11, 17) by the various components of system 2100 (FIG. 1) can include the following list.

| Bioreactor controller | Step# | Step Description |
| --- | --- | --- |
| PREPARATION STAGE | 0 | Critical process parameter initialization |
| | 1 | Set valves to fill from media storage |
| | 2 | Valve handshake |
| | 3 | Fill vessel with final vessel volume + dead volume − compensation volume at 5 vials (padded to 6) |
| | 4 | Stop pumping |
| | 5 | Set valves to Idle |
| | 6 | Valve handshake |
| | 7 | Have user acknowledge dissolved oxygen probe is not connected |
| | 8 | Continue when user acknowledges |
| | 9 | Set dissolved oxygen value for comparison |
| | 10 | Check if the dissolved oxygen signal value has stabilized |
| | 11 | Have user acknowledge dissolved oxygen probe is connected |
| | 12 | Continue when user acknowledges |
| | 13 | Turn on critical process parameter controls |
| | 14 | Confirm valve change occurred and critical process parameters are in range before proceeding |
| | 15 | Wait 10 minutes; if reading is still changing, go back and set next comparison value |

| Bioreactor controller | Step# | Step Description |
|---|---|---|
| | 16 | Switch from 100% $O_2$ to dissolved oxygen control |
| | 17 | Wait for user input |
| SEEDING STAGE | 100 | Message supervisor when ready to flush vials based on type of cells |
| | 101 | Proceed to flushing vial when ready signal arrives |
| | 102 | Set valves to flush vial |
| | 103 | Valve handshake |
| | 104 | Flush vial |
| | 105 | Stop pumping |
| | 106 | Set valves to Idle |
| | 107 | Valve handshake |
| | 108 | Inform supervisor flush has finished |
| | 109 | Get information from supervisor on how to proceed based on whether or not there are more vials to process |
| | 110 | Set valves to fill from media storage |
| | 111 | Valve handshake |
| | 112 | Bring vessel volume up to maximum, accounting for volume added during flush and "burp" volume |
| | 113 | Stop pumping |
| | 114 | Calibrate level sensor setpoint to current value |
| | 115 | Stop Agitation |
| ATTACHMENT STAGE | 200 | Set valves to Idle |
| | 201 | Valve handshake |
| | 202 | Mix cells and microcarriers |
| | 203 | Let cells settle (repeat phase 202 and 203 for 12 hours) |
| | 204 | Turn on agitation |
| CELL GROWTH STAGE | 300 | Set valves to Continuous exchange |
| | 301 | Valve handshake |
| | 302 | Update level sensor value |
| | 303 | Confirm that level sensor is in range |
| | 304 | Set start media exchange pump |
| | 305 | Fill until level sensor setpoint is reached // Check if there are enough cells based on type of cells |
| | 306 | Stop pumping for 5 minutes // Check if there are enough cells based on type of cells (Repeat phases 305 and 306 until desired cell concentration is reached) |
| | 307 | Stop pumping |
| HARVEST STAGE: DRAIN | 400 | Set drain valves |
| | 401 | Valve handshake |
| | 402 | Let cells settle |
| | 403 | Remove supernatant |
| | 404 | Stop pumping |
| HARVEST STAGE: WASH #1 | 500 | Set valves to fill from phosphate buffered saline |
| | 501 | Valve handshake |
| | 502 | Add phosphate buffered saline |
| | 503 | Turn off pumps |
| | 504 | Stir for 30 seconds to mix |
| | 505 | Set drain valves |
| | 506 | Valve handshake |
| | 507 | Wait for cells to settle |
| | 508 | Remove wash media |
| | 509 | Turn off pumps |
| HARVEST STAGE: DIGEST | 600 | Set valves to fill from trypsin |
| | 601 | Valve handshake |
| | 602 | Add trypsin/pectinase |
| | 603 | Stop pumping |
| | 604 | Allow time for sufficient detachment of cells from microcarriers |
| HARVEST STAGE: QUENCH | 700 | Set valves to fill from bone/ligament growth media |
| | 701 | Valve handshake |
| | 702 | Add growth media |
| | 703 | Stop pumping |
| | 704 | Allow time for digestion enzyme to inactivate |
| HARVEST STAGE: FEED 1 | 800 | Set harvest valves |
| | 801 | Valve handshake |
| | 802 | Initiate a first pre-selected recipe sequence |
| | 803 | Wait until first recipe sequence is complete |
| HARVEST STAGE: WASH 2/FEED 2 | 900 | Set valves to fill from phosphate buffered saline |
| | 901 | Valve handshake |
| | 902 | Add phosphate buffered saline |
| | 903 | Stop pumping |
| | 904 | Set valves to fill from growth media |
| | 905 | Valve handshake |
| | 906 | Prime line with bone/ligament growth media |
| | 907 | Stop pumping |
| | 908 | Stir for 30 seconds to mix |
| | 909 | Set valves to harvest |
| | 910 | Valve handshake |

| Bioreactor controller | Step# | Step Description |
|---|---|---|
| | 911 | Initiate a second pre-selected recipe sequence |
| | 912 | Wait until second recipe sequence is complete |
| HARVEST STAGE: PREHARVEST | 1000 | Set valves to fill from growth media |
| | 1001 | Valve handshake |
| | 1002 | Add minimum seeding media |
| | 1003 | Stop pumping |
| | 1004 | Wait for media temperature and pH to be within range |
| HARVEST STAGE: HARVEST | 1100 | Set valves to harvest |
| | 1101 | Valve handshake |
| | 1102 | Initiate a third pre-selected recipe sequence |
| | 1103 | Wait until third recipe sequence is complete |
| HARVEST STAGE: CONCENTRATION ADJUSTMENT | 1200 | Set valves to fill from growth media |
| | 1201 | Valve handshake |
| | 1202 | Add the appropriate volume of growth media to reach the concentration target |
| | 1203 | Stop pumping |
| | 1204 | Wait for media temperature and pH to be within range |
| SEEDING | 1300 | Set valves to harvest |
| | 1301 | Valve handshake |
| | 1302 | Initiate pre-selected seeding sequence based on type of cells |
| | 1303 | Wait for pre-selected sequence to complete based on type of cells |
| | 1401 | Valve handshake |
| | 1402 | Add phosphate buffered saline to wash the insert |
| | 1403 | Stop pumping and agitation |
| | 1404 | Set valves to harvest |
| | 1405 | Valve handshake |
| | 1406 | Initiate a fourth pre-selected recipe sequence |
| | 1407 | Wait until fourth recipe sequence is complete |
| ALARM STATE HANDLING | 8000 | Stop pumps and wait for supervisor to clear error |
| END SCRIPT | 9000 | Shut off bioreactor controller control loops |
| | 9001 | Set valves to Idle |
| | 9002 | Valve handshake |
| | 9999 | End of script hold state |

Various alternatives and modifications can be devised by those skilled in the art without departing from the disclosure. Accordingly, the present disclosure is intended to embrace all such alternatives, modifications and variances. Additionally, while several example configurations of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular configurations. And, those skilled in the art will envision other modifications within the scope and spirit of the claims appended hereto. Other elements, steps, methods and techniques that are insubstantially different from those described above and/or in the appended claims are also intended to be within the scope of the disclosure.

The drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the example configurations of the disclosure described herein are capable of operation in other sequences and/or arrangements than are described or illustrated herein.

What is claimed is:

1. A system for enabling automatic manufacture of tissue comprising:
    a thaw subsystem including a thaw station receiving frozen cells in at least one vial and automatically thawing the frozen cells;
    a thaw controller controlling the preparing of the cells;
    an insulated container and container lid station having a cooling means cooling an environment surrounding the frozen cells in the at least one vial maintaining the frozen cells at a pre-selected temperature range;
    a lid gripper and a vial gripper, the lid gripper moving, under control of the thaw controller, the container lid, the vial gripper moving, under control of the thaw controller, the at least one vial;
    at least one device locating, under control of the thaw controller, a position of each of the at least one vial;
    a decontamination station receiving, from the vial gripper, under control of the thaw controller, the at least one vial of thawed cells, the decontamination station including a means for decontaminating an exterior surface of the at least one vial of thawed cells, thereby forming at least one decontaminated vial of thawed cells;

a puncture station receiving, from the vial gripper, under control of the thaw controller, the at least one decontaminated vial of thawed cells, the puncture station including at least two needles, the at least two needles puncturing, under control of the thaw controller, the at least one decontaminated vial, a first needle of the at least two needles having a first length, a second needle of the at least two needles having a second length, the puncture station including a needle controller puncturing, under control of the thaw controller, the at least one decontaminated vial of thawed cells with the first needle, the first needle extending into the at least one decontaminated vial of thawed cells a first pre-selected distance, the needle controller puncturing, under control of a thaw manager, the at least one decontaminated vial of thawed cells with the second needle, the second needle extending into the at least one decontaminated vial of thawed cells a second pre-selected distance; and a solution pump pumping, under control of the thaw controller, solution from a solution reservoir through solution tubing and the first needle into the at least one decontaminated vial of thawed cells, the thawed cells being drawn through the second needle, the thawed cells flowing through cell tubing into a cell reservoir, the cells being removed from the at least one decontaminated vial of thawed cells creating at least one waste vial, wherein the thaw station is configured to receive, from the vial gripper, under control of the thaw controller, the at least one located vial, the thaw station including a thawing device housing the at least one located vial, the thawing device thawing the cells within the at least one vial, the thaw station including a thaw station controller, under control of the thaw controller, the thaw station controller providing a status of the cells to the thaw controller;

an expansion subsystem automatically pumping cells from at least one vial to at least one first bioreactor, the expansion subsystem automatically shutting valves from the at least one vial to the at least one first bioreactor when the cells are moved to the at least one first bioreactor, the expansion subsystem automatically creating a first pre-selected environment promoting expansion of the cells in the at least one first bioreactor, the expansion subsystem automatically pumping the expanded cells from the at least one first bioreactor to a concentrator when the expanded cells have reached a pre-selected density, the expansion subsystem configured to create resuspended cells from concentrated cells;

a concentration subsystem automatically concentrating the expanded cells; and a maturation subsystem automatically pumping the resuspended cells into at least one second bioreactor when a pre-selected event has occurred, the maturation subsystem automatically creating a second pre-selected environment promoting maturation of the concentrated cells in the at least one second bioreactor based on monitoring sensor data of critical process parameters.

2. The system as in claim 1 wherein the concentration subsystem comprises a centrifugation device.

3. The system as in claim 1 wherein the pre-selected event comprises a detection of a desired concentration.

4. The system as in claim 1 wherein the first pre-selected environment comprises a first growth media, the first growth media being continuously automatically adjusted based on monitoring sensor data of the critical process parameters to maintain first pre-selected levels of growth media characteristics.

5. The system as in claim 1 wherein the second pre-selected environment comprises second growth media, the second growth media being continuously automatically adjusted based on monitoring of sensor data of the critical process parameters to maintain second pre-selected levels of growth media characteristics.

6. The system as in claim 1 further comprising:
an identification station identifying, under control of the thaw controller, each of the at least one vial.

7. The system as in claim 1 wherein the first length comprises a longer length than the second length.

8. The system as in claim 1 wherein the first pre-selected distance comprises a shorter distance than the second pre-selected distance.

9. The system as in claim 1 comprising a gas purge forcing substantially all contents of the at least one decontaminated vial to exit the at least one decontaminated vial.

10. The system as in claim 1 wherein the decontamination station comprises:
a hood retaining decontamination fluids within a pre-selected area surrounding the located at least one vial of thawed cells;
a decontamination pump pumping, under control of the thaw controller, the decontamination fluids into the pre-selected area; and
a nozzle directing the decontamination fluids towards the at least one located vial of thawed cells.

11. The system as in claim 1 wherein the puncture station comprises:
a base gripper maintaining the at least one located vial in place while the needle controller, under control of the thaw controller, removes the first needle and the second needle.

12. The system as in claim 1 further comprising:
a waste system receiving, from the vial gripper, under control of the thaw controller, the at least one waste vial after the needle controller removes the first needle and the second needle, the waste system depositing the at least one waste vial into a waste receptacle.

13. The system as in claim 1 further comprising:
a hood surrounding the puncture station, the hood maintaining a controlled, clean volume surrounding the puncture station.

14. The system as in claim 1 wherein the expansion subsystem comprises:
an expansion controller controlling a flow of cells from a thaw subsystem to the expansion subsystem; and
a bioreactor controller monitoring and modifying the first pre-selected environment.

15. The system as in claim 14 wherein the bioreactor controller comprises:
an agitation controller agitating the cells to encourage attachment of the cells to a surface;
a temperature controller adjusting temperature of the at least one first bioreactor based on a pre-selected desired temperature;
a gas mixing processor adjusting levels of gas in media surrounding the cells, the levels of gas based on pre-selected desired values of characteristics of the media;
a monitoring process sensing values of the characteristics of the media; and a pump controller moving the media to and from the at least one first bioreactor.

16. The system as in claim 15 wherein the characteristics comprise dissolved oxygen and pH.

17. The system as in claim 1 wherein the maturation subsystem comprises:
   a media controller monitoring and modifying media before introducing the media to the second at least one bioreactor; and
   an incubator controller managing movement of the at least one second bioreactor, the incubator controller monitoring characteristics of the media in the at least one second bioreactor, the incubator controller flushing and restoring media from/to the at least one second bioreactor.

18. The system as in claim 1 further comprising a media storage controller comprising:
   a media level sensor monitoring an amount of media in a media reservoir; and
   a pump pressure sensor monitoring a pump moving media from the media reservoir to a media vessel.

* * * * *